United States Patent
Kawasumi et al.

(10) Patent No.: US 11,024,882 B2
(45) Date of Patent: Jun. 1, 2021

(54) ELECTROLYTIC SOLUTION FOR SECONDARY BATTERY, SECONDARY BATTERY, BATTERY PACK, ELECTRICALLY DRIVEN VEHICLE, POWER STORAGE SYSTEM, ELECTRICALLY DRIVEN TOOL, AND ELECTRONIC DEVICE

(71) Applicant: MURATA MANUFACTURING CO., LTD., Kyoto (JP)

(72) Inventors: Katsuaki Kawasumi, Kyoto (JP); Toru Odani, Kyoto (JP); Kazumasa Takeshi, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 42 days.

(21) Appl. No.: 16/380,583

(22) Filed: Apr. 10, 2019

(65) Prior Publication Data
US 2019/0237806 A1   Aug. 1, 2019

Related U.S. Application Data

(63) Continuation of application No. PCT/JP2017/036643, filed on Oct. 10, 2017.

(30) Foreign Application Priority Data

Nov. 9, 2016 (JP) .............................. JP2016-218625

(51) Int. Cl.
*H01M 10/0525* (2010.01)
*H01M 10/0567* (2010.01)
(Continued)

(52) U.S. Cl.
CPC ....... *H01M 10/0567* (2013.01); *C07C 315/04* (2013.01); *C08F 132/08* (2013.01);
(Continued)

(58) Field of Classification Search
CPC ......... H01M 10/0567; H01M 10/0525; H01M 10/054; H01M 10/0569; H01M 10/44;
(Continued)

(56) References Cited

U.S. PATENT DOCUMENTS

2007/0224514 A1* 9/2007 Kotato ............. H01M 10/0525
429/325
2009/0325065 A1* 12/2009 Fujii ................. H01M 10/0568
429/199
(Continued)

FOREIGN PATENT DOCUMENTS

JP   2006049112 A   2/2006
JP   2006049152 A   2/2006
(Continued)

OTHER PUBLICATIONS

Decision to grant a patent for Application No. 2016-218625 (Year: 2019).*

(Continued)

*Primary Examiner* — Alexander Usyatinsky
(74) *Attorney, Agent, or Firm* — K&L Gates LLP

(57) ABSTRACT

A secondary battery includes a positive electrode, a negative electrode, and an electrolytic solution including at least one of sulfonyl compounds expressed by $R(-S(=O)_2-Rf)_n$, where R represents an n-valent hydrocarbon group including one or two or more aliphatic hydrocarbon rings, Rf includes one of a halogen group and a monovalent halogenated hydrocarbon group, n is an integer greater than or equal to 1.

18 Claims, 6 Drawing Sheets

(51) Int. Cl.
*H01M 10/0569* (2010.01)
*H01M 10/054* (2010.01)
*H01M 4/48* (2010.01)
*H01M 10/44* (2006.01)
*C07C 315/04* (2006.01)
*C08G 61/04* (2006.01)
*C08F 132/08* (2006.01)
*H01M 10/48* (2006.01)
*H01M 50/20* (2021.01)
*H01M 4/02* (2006.01)

(52) U.S. Cl.
CPC .............. *C08G 61/04* (2013.01); *H01M 4/48* (2013.01); *H01M 10/054* (2013.01); *H01M 10/0525* (2013.01); *H01M 10/0569* (2013.01); *H01M 10/44* (2013.01); *H01M 10/48* (2013.01); *H01M 50/20* (2021.01); *H01M 2004/027* (2013.01); *H01M 2004/028* (2013.01); *H01M 2300/0025* (2013.01); *Y02E 60/10* (2013.01); *Y02T 10/70* (2013.01)

(58) Field of Classification Search
CPC .......... H01M 10/48; H01M 2/10; H01M 4/48; H01M 2004/028; H01M 2004/027; H01M 2300/0025; C07C 315/04; C08F 132/08; C08G 61/04; C08G 2261/3221; C08G 73/0266; C08G 2261/3223; C08G 2261/512; Y02E 60/122; Y02T 10/7011
See application file for complete search history.

(56) References Cited

U.S. PATENT DOCUMENTS

| | | | |
|---|---|---|---|
| 2012/0316716 A1* | 12/2012 | Odani | H01M 10/0568 701/22 |
| 2014/0017559 A1* | 1/2014 | Kawasaki | H01M 10/0569 429/200 |
| 2014/0234729 A1 | 8/2014 | Kanazawa et al. | |
| 2015/0064549 A1* | 3/2015 | Pinnell | H01M 10/0567 429/163 |
| 2015/0188193 A1 | 7/2015 | Kodama et al. | |
| 2015/0266816 A1 | 9/2015 | Takahashi et al. | |

FOREIGN PATENT DOCUMENTS

| | | |
|---|---|---|
| JP | 2009054288 A | 3/2009 |
| JP | 2009054407 A | 3/2009 |
| JP | 2009054408 A | 3/2009 |
| JP | 2013110102 A | 6/2013 |
| JP | 2014063596 A | 4/2014 |
| JP | 2014111569 A | 6/2014 |

OTHER PUBLICATIONS

International Search Report for Application No. PCT/JP2017/036643, dated Nov. 14, 2017.

* cited by examiner

ELECTROLYTIC SOLUTION FOR SECONDARY BATTERY, SECONDARY BATTERY, BATTERY PACK, ELECTRICALLY DRIVEN VEHICLE, POWER STORAGE SYSTEM, ELECTRICALLY DRIVEN TOOL, AND ELECTRONIC DEVICE

CROSS REFERENCE TO RELATED APPLICATIONS

The present application is a continuation of PCT patent application no. PCT/JP2017/036643, filed on Oct. 10, 2017, which claims priority to Japanese patent application no. JP2016-218625 filed on Nov. 9, 2016, the entire contents of which are being incorporated herein by reference.

BACKGROUND

The technology generally disclosed herein relates to an electrolytic solution for use in secondary batteries, a secondary battery using the electrolytic solution, a battery pack using the secondary battery, an electrically driven vehicle, a power storage system, an electrically driven tool, and an electronic device.

A diverse range of electronic devices is becoming widespread, which includes mobile telephones and personal digital assistants (PDA). Such electronic devices are desirably further reduced in size and weight and improved in product life. To this end, batteries, especially, light, small-sized secondary batteries that can provide higher energy densities are being developed as power source for such electronic devices.

Besides use in the electronic devices described earlier, other possible applications of the secondary battery are being discussed. They are, for example, battery packs removably mounted in electronic devices, electrically driven vehicles such as electric automobiles, power storage systems for home power servers, and electrically driven tools such as electric drills.

The secondary battery includes a positive electrode and a negative electrode, and further includes an electrolytic solution. The compositional characteristic of the electrolytic solution that may have large impacts on properties of the battery have been and are being studied and discussed from a number of different aspects.

SUMMARY

Electronic devices are growingly sophisticated in performance and functionally diversified. As such, the electronic devices are more and more heavily used in an increasing number of occasions and environments. Under the circumstances, there is still room for improvements with properties of the secondary battery.

It is desirable, therefore, to provide an electrolytic solution for use in secondary batteries that allow the batteries to acquire remarkable properties, and also to provide a secondary battery, a battery pack, an electrically driven vehicle, a power storage system, an electrically driven tool, and an electronic device accordingly improved in performance.

According to an embodiment of the present technology, an electrolytic solution for secondary battery is provided. The electrolytic solution includes at least one of sulfonyl compounds expressed by chemical formula (1):

[Chemical Formula 1]

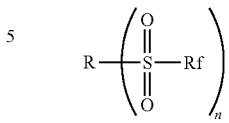

(1)

(where R represents an n-valent hydrocarbon group including one or two or more aliphatic hydrocarbon rings, Rf includes one of a halogen group and a monovalent halogenated hydrocarbon group, n is an integer greater than or equal to 1.

According to an embodiment of the present technology, a secondary battery is provided. The secondary battery includes a positive electrode, a negative electrode, and an electrolytic solution. The electrolytic solution is formulated into a composition similar to that of the electrolytic solution for secondary battery according to the embodiment as described herein.

A battery pack, an electrically driven vehicle, a power storage system, an electrically driven tool, and an electronic device according to an embodiment of the technology disclosed herein each include a secondary battery. The secondary battery has a configuration similar to that of the secondary battery according to the embodiment as described herein.

The "n-valent hydrocarbon group" is a generic term that refers to n-valent groups each including carbon (C) and hydrogen (H) and further including one or two or more aliphatic hydrocarbon rings.

The aliphatic hydrocarbon ring may or may not include one or two or more carbon-carbon unsaturated bonds (one or both of carbon-carbon double bond and carbon-carbon triple bond). The aliphatic hydrocarbon ring may be either monocyclic or polycyclic according embodiments of the present technology.

The n-valent hydrocarbon group may solely consist of one or two or more aliphatic hydrocarbon rings, or may include one or two or more aromatic hydrocarbon rings in addition to the one or two or more aliphatic hydrocarbon rings according embodiments of the present technology.

In the n-valent hydrocarbon group including one or two or more aliphatic hydrocarbon rings and further including one or two or more aromatic hydrocarbon rings, a ring closest to a sulfur atom forming a sulfonyl group is not an aromatic hydrocarbon ring but is an aliphatic hydrocarbon ring.

The n-valent hydrocarbon group may be a group including one aliphatic hydrocarbon ring, a group including two or more aliphatic hydrocarbon rings, a group in which one or two or more aliphatic hydrocarbon rings and one or two or more aliphatic hydrocarbon chains are bonded to each other, or any one of the before-mentioned groups in which one or two or more aromatic hydrocarbon rings are introduced as a substituent group(s). When the n-valent hydrocarbon group is a group including two or more aliphatic hydrocarbon rings, the two or more aliphatic hydrocarbon rings may preferably be bonded to each other.

In Chemical Formula (1), the sulfur atom forming the sulfonyl group may be bonded to a carbon atom forming the aliphatic hydrocarbon ring in the R or may be bonded to another carbon atom uninvolved in the formation of the aliphatic hydrocarbon ring. The "another carbon atom" is a carbon atom forming the one or two or more aliphatic hydrocarbon chains.

The "monovalent halogenated hydrocarbon group" is a group obtained by substituting one or two or more hydrogen groups (—H) of a monovalent hydrocarbon group with a halogen group(s). The "monovalent hydrocarbon group" is a generic term that refers to monovalent groups each including carbon and hydrogen. The "monovalent hydrocarbon group" may be a straight chain group, a branched group having one or two or more side chains, a cyclic group, or a group in which two or more of the before-mentioned groups are bonded to each other. When the number of the halogen groups is two or more, the two or more halogen groups may be of a single type or two or more different types.

The "monovalent halogenated hydrocarbon group" may or may not include one or two or more carbon-carbon unsaturated bonds. The "monovalent halogenated hydrocarbon group" may have aliphatic properties (non-aromatic properties) or may have aromatic properties.

According to the electrolytic solution for secondary battery or the secondary battery provided by the one embodiment of the technology disclosed herein, the electrolytic solution containing the sulfonyl compound described earlier may allow the secondary battery to excel in properties. Similar effects, therefore, may be obtained with the battery pack, electrically driven vehicle, power storage system, electrically driven tool, and electronic device according to the one embodiment of the technology disclosed herein.

The effects described herein are only given by way of example, and any optional one(s) of such effects may be achieved by the technology disclosed herein.

DETAILED DESCRIPTION

Figure 1:
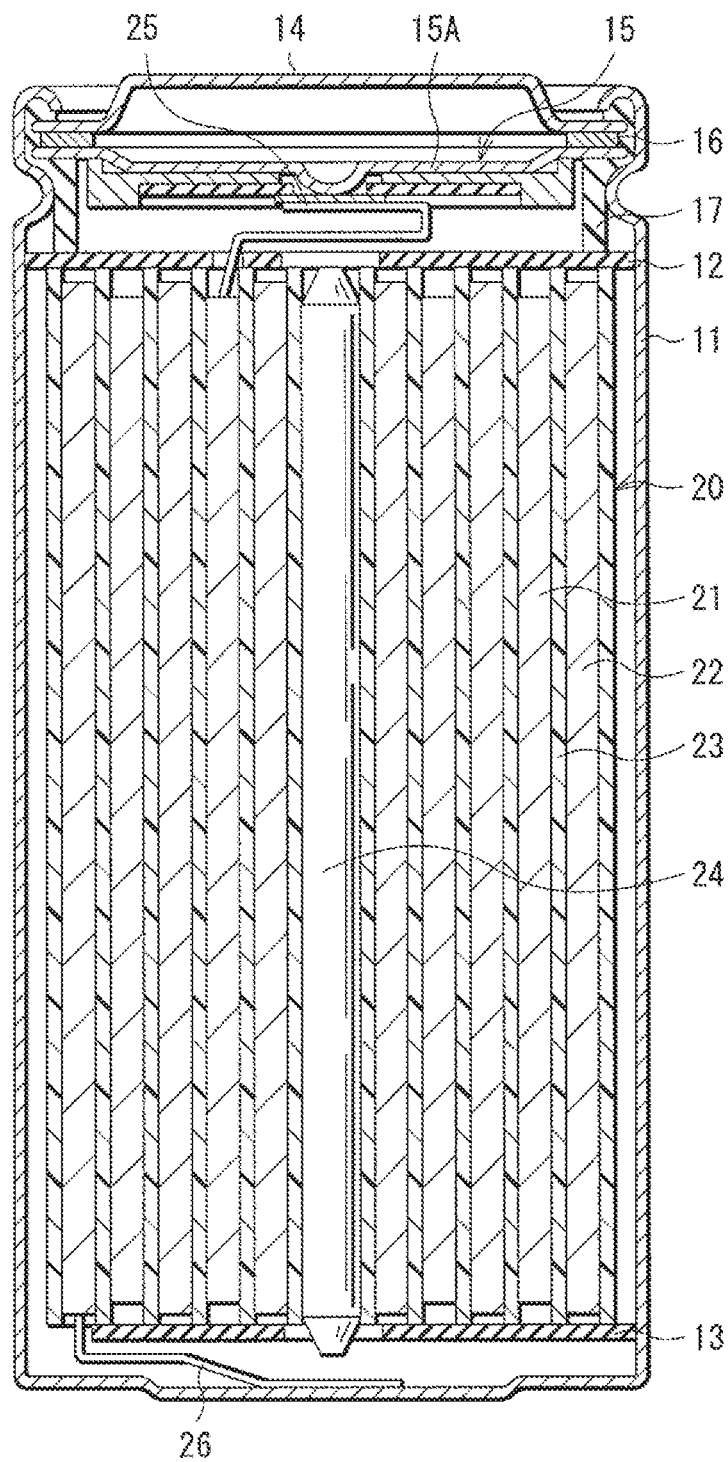
FIG. 1 is a cross-sectional view of a secondary battery (cylindrical battery) according to an embodiment of the technology disclosed herein.

As described herein, the present disclosure will be described based on examples with reference to the drawings, but the present disclosure is not to be considered limited to the examples, and various numerical values and materials in the examples are considered by way of example.

First, an electrolytic solution for secondary battery according to one embodiment of the technology disclosed herein is hereinafter described.

The electrolytic solution for secondary battery (hereinafter, simply referred to as "electrolytic solution") described herein is for use in secondary batteries including lithium ion secondary batteries. The electrolytic solution, however, is not limitedly applicable to lithium ion secondary batteries alone.

The electrolytic solution contains one or two or more of sulfonyl compounds expressed by the Chemical Formula (1). Thus, a single type of or two or more different types of sulfonyl compounds may be optionally added to the electrolytic solution.

[Chemical Formula 1]

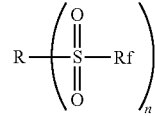

(1)

(where R represents an n-valent hydrocarbon group including one or two or more aliphatic hydrocarbon rings, Rf is one of a halogen group and a monovalent halogenated hydrocarbon group, n is an integer greater than or equal to 1, and the n-valent hydrocarbon group may include one or two or more aromatic hydrocarbon rings, provided that a ring closest to a sulfur atom forming a sulfonyl group is an aliphatic hydrocarbon ring).

In this sulfonyl compound, one or two or more branches including a sulfonyl group (—S(=O)$_2$—Rf) are bonded to a stem (R) including one or more aliphatic hydrocarbon rings.

The electrolytic solution contains a sulfonyl compound because this compound improves chemical stability of the electrolytic solution. This may inhibit possible decomposition reactions of the electrolytic solution and may reduce the risk of gases being produced from the decomposed electrolytic solution, thereby improving properties of a secondary battery in which the electrolytic solution is used. When, for example, the secondary battery is used (discharged and charged) and stored in severe environments at extremely high or low temperatures, the electrolytic solution may be unlikely to decompose and may succeed in preventing production of gases. As a result, the secondary battery may be markedly improved in properties.

Specifics of the sulfonyl compound expressed by Formula (1) are described below.

As described earlier, R represents an n-valent hydrocarbon group. The "n-valent hydrocarbon group" is, as described earlier, a generic term that refers to n-valent groups each including carbon and hydrogen and further including one or two or more aliphatic hydrocarbon rings. The aliphatic hydrocarbon ring may or may not include one or two or more carbon-carbon unsaturated bonds (one or both of carbon-carbon double bond and carbon-carbon triple bond). The aliphatic hydrocarbon ring may be either monocyclic or polycyclic.

The n-valent hydrocarbon group may solely consist of one or two or more aliphatic hydrocarbon rings, or may include one or two or more aromatic hydrocarbon rings in addition to the one or two or more aliphatic hydrocarbon rings. In the n-valent hydrocarbon group including one or two or more aliphatic hydrocarbon rings and further including one or two or more aromatic hydrocarbon rings, a ring closest to a sulfur atom forming a sulfonyl group is not an aromatic hydrocarbon ring but is an aliphatic hydrocarbon ring.

Whether or not to meet the condition, "a ring closest to a sulfur atom forming a sulfonyl group is not an aromatic hydrocarbon ring but is an aliphatic hydrocarbon ring", is specifically defined below. Firstly, when the sulfur atom is directly bonded to an aliphatic hydrocarbon ring, for example, a ring in the R closest to the sulfur atom is an aliphatic hydrocarbon ring, which meets the condition. Secondary, when the sulfur atom is directly bonded to an aromatic hydrocarbon ring, for example, a ring in the R closest to the sulfur atom is an aromatic hydrocarbon ring, which does not meet the condition. Thirdly, when the sulfur atom is bonded to an aliphatic hydrocarbon ring through an aliphatic hydrocarbon chain as described later, for example, a ring in the R closest to the sulfur atom is an aliphatic hydrocarbon ring, which meets the condition. Fourthly, when the sulfur atom is bonded to an aromatic hydrocarbon ring through an aliphatic hydrocarbon difference, for example, a ring in the R closest to the sulfur atom is an aromatic hydrocarbon ring, which does not meet the condition.

When a ring closest to the sulfur atom forming a sulfonyl group is an aliphatic hydrocarbon ring, the electrolytic solution may improve in chemical stability, in contrast to the closest ring being an aromatic hydrocarbon ring. This may inhibit possible decomposition reactions of the electrolytic solution and may prevent the risk of gases being produced from the decomposed electrolytic solution, thereby improving properties of a secondary battery in which the electrolytic solution is used.

The n-valent hydrocarbon group may be a group including one aliphatic hydrocarbon ring, a group including two or more aliphatic hydrocarbon rings, a group in which one or two or more aliphatic hydrocarbon rings and one or two or more aliphatic hydrocarbon chains are bonded to each other, or any one of the before-mentioned groups in which one or two or more aromatic hydrocarbon rings are introduced as a substituent group(s). Details of the substituent group will be given later. When the n-valent hydrocarbon group is a group including two or more aliphatic hydrocarbon rings, the two or more aliphatic hydrocarbon rings may preferably be bonded to each other.

The n-valent hydrocarbon group may or may not include one or two or more aromatic hydrocarbon rings. While the aromatic hydrocarbon ring is not particularly limited to any specific type of ring, examples of the aromatic hydrocarbon ring may include benzene ring and naphthalene ring.

It may be preferable for the n-valent hydrocarbon group not to include one or two or more aromatic hydrocarbon rings. Specifically, the n-valent hydrocarbon group may preferably solely consist of one or two or more aliphatic hydrocarbon rings, or may include one or two or more aliphatic hydrocarbon chains in addition to the one or two or more aliphatic hydrocarbon rings. This may further improve chemical stability of the electrolytic solution, effectively reducing the risk of the electrolytic solution being decomposed.

In Chemical Formula (1), the sulfur atom forming the sulfonyl group may be bonded to a carbon atom forming the aliphatic hydrocarbon ring in the R, or may be bonded to another carbon atom uninvolved in the formation of the aliphatic hydrocarbon chain. The "another carbon atom" is a carbon atom forming the one or two or more aliphatic hydrocarbon chains.

In particular, the sulfur atom may preferably be bonded to a carbon atom forming the aliphatic hydrocarbon ring. Specifically, the sulfur atom and the carbon atom may preferably be directly bonded to each other in the absence of any aliphatic hydrocarbon chain between these atoms. This may even further improve chemical stability of the electrolytic solution, more effectively reducing the risk of the electrolytic solution being decomposed.

As is clearly known from Chemical Formula (1), the valence of the stem (R: n-valent hydrocarbon group) is variably decided in accordance with the number of branches ($-S(=O)_2-Rf$) (value of n). For example, the valence of the stem (n-valent hydrocarbon group) is 1 in the case of one branch (n=1). Likewise, the valence of the stem is 2 in the case of two branches (n=2). The valence of the stem is 3 in the case of three branches is 3 (n=3). Naturally, the valence of the stem may be 4 or more with an increasing number of branches.

The n-valent hydrocarbon group may preferably be a group with a distorted carbon skeleton, like a group obtained by eliminating n number of hydrogen groups from a polycyclic hydrocarbon compound which will be described later, instead of a group with an undistorted carbon skeleton obtained by eliminating n number of hydrogen groups from alkane. Such a group may be preferable because it allows the electrolytic solution to further improve in chemical stability.

A specific example of the n-valent hydrocarbon group may be any one selected from the groups listed below.

(A) n-valent group including one monocyclic aliphatic hydrocarbon ring, (B) n-valent group including one polycyclic aliphatic hydrocarbon ring, (C) n-valent group in which two or more monocyclic aliphatic hydrocarbon rings are bonded to each other, (D) n-valent group in which two or more polycyclic aliphatic hydrocarbon rings are bonded to each other, (E) n-valent group in which one or more monocyclic aliphatic hydrocarbon rings and one or more polycyclic aliphatic hydrocarbon rings are bonded to each other, (F) n-valent group in which one or more monocyclic aliphatic hydrocarbon rings and one or more aliphatic hydrocarbon chains are bonded to each other, (G) n-valent group in which one or more polycyclic aliphatic hydrocarbon rings and one or more aliphatic hydrocarbon chains are bonded to each other, and (H) n-valent group in which one or more monocyclic aliphatic hydrocarbon rings, one or more polycyclic aliphatic hydrocarbon rings, and one or more aliphatic hydrocarbon chains are bonded to one another.

The "n-valent group including one monocyclic aliphatic hydrocarbon ring" is an n-valent hydrocarbon group with one monocyclic ring (monocyclic aliphatic hydrocarbon ring).

A monovalent hydrocarbon group including one monocyclic ring may be a group obtained by eliminating one hydrogen group from any one of cycloalkane, cycloalkene, cycloalkyne, and compounds in which two or more of cycloalkane, cycloalkene, and cycloalkyne are combined. A position at which the hydrogen group is eliminated is not particularly limited. Likewise, no limitation may be imposed on hydrogen group-eliminating positions in all of the examples hereinafter described.

Examples of the cycloalkane may include but are not limited to cyclopropane, cyclobutane, cyclopentane, cyclohexane, cycloheptane, cyclooctane, cyclononane, and cyclodecane.

The group obtained by eliminating one hydrogen group from cycloalkane is a generally called cycloalkyl group. Examples of the cycloalkyl group may include but are not limited to cyclopropyl group, cyclobutyl group, cyclopentyl group, cyclohexyl group, cycloheptyl group, cyclooctyl group, cyclononyl group, and cyclodecyl group.

Examples of the cycloalkene may include but are not limited to cyclopropene, cyclobutene, cyclopentene, cyclohexene, cycloheptene, cyclooctene, cyclononene, and cyclodecene.

The group obtained by eliminating one hydrogen group from cycloalkene is a generally called cycloalkenyl group. Examples of the cycloalkenyl group may include but are not limited to cyclopropenyl group, cyclobutenyl group, cyclopentenyl group, cyclohexenyl group, cycloheptenyl group, cyclooctenyl group, cyclononenyl group, and cyclodecenyl group.

Examples of the cycloalkyne may include but are not limited to cyclopropyne, cyclobutyne, cyclopentyne, cyclohexyne, cycloheptyne, cyclooctyne, cyclononyne, and cyclodecyne.

The group obtained by eliminating one hydrogen group from cycloalkyne is a generally called cycloalkynyl group. Examples of the cycloalkynyl group may include but are not limited to cyclopropynyl group, cyclobutynyl group, cyclopentynyl, group cyclohexynyl group, cycloheptynyl group, cyclooctynyl group, cyclononylyl group, and cyclodecynyl group.

A bivalent hydrocarbon group including one monocyclic ring may be a group obtained by eliminating two hydrogen groups from any one of the cycloalkane, cycloalkene, cycloalkyne, and compounds in which two or more of cycloalkane, cycloalkene, and cycloalkyne are combined.

The group obtained by eliminating two hydrogen groups from cycloalkane is a generally called cycloalkylene group. Examples of the cycloalkylene group may include but are not limited to cyclopropylene group, cyclobutylene group, cyclopentylene group, cyclohexylene group, cycloheptylene group, cyclooctylene group, cyclononylene group, and cyclodecylene group.

The group obtained by eliminating two hydrogen groups from cycloalkene is a generally called cycloalkenylene group. Examples of the cycloalkenylene group may include but are not limited to cyclopropenylene group, cyclobutenylene group, cyclopentenylene group, cyclohexenylene group, cycloheptenylene group, cyclooctenylene group, cyclononenylene group, and cyclodecenylene group.

The group obtained by eliminating two hydrogen groups from cycloalkyne may be a generally called cycloalkynylene group. Examples of the cycloalkynylene group may include but are not limited to cyclopropynylene group, cyclobutynylene group, cyclopentynylene group, cyclohexynylene group, cycloheptynylene group, cyclooctynylene group, cyclononylylene group, and cyclodecynylene group.

A trivalent hydrocarbon group including one monocyclic ring may be a group obtained by eliminating three hydrogen groups from any one of the cycloalkane, cycloalkene, cycloalkyne, and compounds in which two or more of cycloalkane, cycloalkene, and cycloalkyne are combined.

It should be understood that the n-valent hydrocarbon group including one monocyclic ring may be a tetravalent or higher multivalent hydrocarbon group including one monocyclic ring.

When the n-valent hydrocarbon group includes one monocyclic ring (monocyclic aliphatic hydrocarbon ring), the number of carbons in the monocyclic aliphatic hydrocarbon ring, though not particularly limited, may preferably be between 3 and 12, more preferably between 3 and 8, and even more preferably 3 or 4. This may provide markedly improved chemical stability of the electrolytic solution, while ensuring solubility and compatibility of the sulfonyl compound.

The "n-valent group including one polycyclic aliphatic hydrocarbon ring" is an n-valent hydrocarbon group with one polycyclic ring (polycyclic aliphatic hydrocarbon ring).

A monovalent hydrocarbon group including one polycyclic ring may be a group obtained by eliminating one hydrogen group from any one of a spiro polycyclic compound, a condensation polycyclic compound, a polycyclic hydrocarbon-based polycyclic compound, and compounds in which two or more of these compounds are combined.

The "spiro polycyclic compound" is a compound in which two adjacent aliphatic hydrocarbon rings are bonded to each other through one common carbon atom (spiro atom). Examples of the spiro polycyclic compound may include but are not limited to spiropentadiene and spiroundecane. The spiro polycyclic compound may contain two or three or more aliphatic hydrocarbon rings.

The "condensation polycyclic compound" is a compound in which two adjacent aliphatic hydrocarbon rings are bonded to each other through two common carbon atoms. Examples of the condensation polycyclic compound may include but are not limited to decahydronaphthalene and bicycloundecane.

The "polycyclic hydrocarbon-based polycyclic compound" is a compound in which two or more aliphatic hydrocarbon rings are bonded to form a three-dimensional structure. Examples of the polycyclic hydrocarbon-based polycyclic compound may include but are not limited to norbornane, norbornene, norbornadiene, adamantane, cubane, basketane, and housane.

A bivalent hydrocarbon group including one polycyclic ring may be a group obtained by eliminating two hydrogen groups from any one of a spiro polycyclic compound, a condensation polycyclic compound, a polycyclic hydrocarbon-based polycyclic compound, and compounds in which two or more of these compounds are combined.

A trivalent hydrocarbon group including one polycyclic ring may be a group obtained by eliminating two hydrogen groups from any one of a spiro polycyclic compound, a condensation polycyclic compound, a polycyclic hydrocarbon-based polycyclic compound, and compounds in which two or more of these compounds are combined.

It should be understood that the n-valent hydrocarbon group including one polycyclic ring may be a tetravalent or higher multivalent hydrocarbon group including one polycyclic ring.

The "n-valent group in which two or more monocyclic aliphatic hydrocarbon rings are bonded to each other" is an n-valent hydrocarbon group in which two or more monocyclic rings (monocyclic aliphatic hydrocarbon ring) are joined to each other by a single bond.

The n-valent hydrocarbon group may contain two or three or more monocyclic rings. When the n-valent hydrocarbon group includes three or more monocyclic rings, adjacent ones of the monocyclic rings are joined to each other by a single bond. The two or more monocyclic rings may be of a single type or two or more different types.

A monovalent hydrocarbon group in which two or more monocyclic rings are joined to each other by a single bond may be a group obtained by eliminating one hydrogen group from a single bond monocyclic compound.

The "single bond monocyclic compound" is a compound in which one carbon atom in one of two adjacent monocyclic rings is single bonded to one carbon atom in the other monocyclic ring. Examples of the single bond monocyclic compound may include but are not limited to cyclopropylcyclopropane, cyclobutylcyclobutane, cyclopropylcyclobutane, cyclopentylcyclopentane, cyclopentylcyclohexane, cyclohexylcyclohexane, cyclooctylcyclooctane, cyclononylcyclononane, and cyclodecylcyclodecane.

A bivalent hydrocarbon group in which two or more monocyclic rings are joined to each other by a single bond may be a group obtained by eliminating two hydrogen groups from a single bond monocyclic compound.

A trivalent hydrocarbon group in which two or more monocyclic rings are joined to each other by a single bond may be a group obtained by eliminating two hydrogen groups from a single bond monocyclic compound.

It should be understood that the n-valent hydrocarbon group in which two or more monocyclic rings are joined to each other by a single bond may be a tetravalent or higher multivalent hydrocarbon group in which two or more monocyclic rings are joined to each other by a single bond.

The "n-valent group including two or more polycyclic aliphatic hydrocarbon rings are bonded to each other" is an n-valent hydrocarbon group in which two or more polycyclic rings (polycyclic aliphatic hydrocarbon ring) are joined to each other by a single bond.

The n-valent hydrocarbon group may contain two or three or more polycyclic rings. When the n-valent hydrocarbon group includes three or more polycyclic rings, adjacent ones of the polycyclic rings are joined to each other by a single bond. The two or more polycyclic rings may be of a single type or two or more different types.

A monovalent hydrocarbon group in which two or more polycyclic rings are joined to each other by a single bond may be a group obtained by eliminating one hydrogen group from a single bond polycyclic compound.

The "single bond polycyclic compound" is a compound in which one carbon atom in one of two adjacent polycyclic rings is single bonded to one carbon atom in the other polycyclic ring.

Examples of the single bond polycyclic compound may include a compound containing spiro polycyclic compounds that are combined by a single bond, a compound containing condensation polycyclic compounds that are combined by a single bond, a compound containing polycyclic hydrocarbon-based polycyclic compounds that are combined by a single bond, a compound containing a spiro polycyclic compound and a condensation polycyclic compound that are combined by a single bond, a compound containing a spiro polycyclic compound and a polycyclic hydrocarbon-based polycyclic compound that are combined by a single bond, a compound containing a condensation polycyclic compound and a polycyclic hydrocarbon-based polycyclic compound that are combined by a single bond, a compound containing a spiro polycyclic compound, a condensation polycyclic compound, and a polycyclic hydrocarbon-based polycyclic compound that are combined by a single bond. The single bond polycyclic compound may contain a single type of or two or more different types of the spiro polycyclic compounds, condensation polycyclic compounds, and/or polycyclic hydrocarbon-based polycyclic compounds.

Specific examples of the single bond polycyclic compound may include but are not limited to a compound in which spiropentadiene and decahydronaphthalene are joined to each other by a single bond, a compound in which spiropentadiene and adamantane are joined to each other by a single bond, a compound in which decahydronaphthalene and adamantane are joined to each other by a single bond, and a compound in which spiropentadiene, decahydronaphthalene, and adamantane are joined to one another by a single bond.

A bivalent hydrocarbon group in which two or more polycyclic rings are joined to each other by a single bond may be a group obtained by eliminating two hydrogen groups from a single bond polycyclic compound.

A trivalent hydrocarbon group in which two or more polycyclic rings are joined to each other by a single bond may be a group obtained by eliminating three hydrogen groups from a single bond polycyclic compound.

It should be understood that the n-valent hydrocarbon group in which two or more polycyclic rings are joined to each other by a single bond may be a tetravalent or higher multivalent hydrocarbon group in which two or more polycyclic rings are joined to each other by a single bond.

The "n-valent group in which one or more monocyclic aliphatic hydrocarbon rings and one or more polycyclic aliphatic hydrocarbon rings are bonded to each other" is an n-valent hydrocarbon group in which one or more monocyclic rings (monocyclic aliphatic hydrocarbon ring) and one or more polycyclic rings (polycyclic aliphatic hydrocarbon ring) are joined to each other by a single bond.

The n-valent hydrocarbon group may contain one or two or more monocyclic rings. Likewise, n-valent hydrocarbon group may contain one or two or more polycyclic rings. When the n-valent hydrocarbon group includes two or more monocyclic rings or two or more polycyclic rings, adjacent ones of the monocyclic and polycyclic rings are joined to each other by a single bond.

When the number of the monocyclic rings is two or more, the two or more monocyclic rings may be of a single type or two or more different types. Likewise, when the number of the polycyclic rings is two or more, the two or more polycyclic rings may be of a single type or two or more different types.

The order of bonds that occur between one or more monocyclic rings and one or more polycyclic rings is not particularly limited and may optionally follow any sequential order.

In the case of one monocyclic ring and two polycyclic rings, for example, a single bond may occur in the order of the monocyclic ring, polycyclic ring, and polycyclic ring, or may occur in the order of polycyclic ring, monocyclic ring, and polycyclic ring. In the case of two monocyclic rings and two polycyclic rings, for example, a single bond may occur in any one of the following orders: monocyclic, monocyclic, polycyclic, and polycyclic; monocyclic, polycyclic, monocyclic, and polycyclic; monocyclic, polycyclic, polycyclic, and monocyclic; and polycyclic, monocyclic, monocyclic, and polycyclic.

For example, (A) may be referred to for details of the monocyclic ring (monocyclic aliphatic hydrocarbon ring). For example, (B) may be referred to for details of the polycyclic ring (polycyclic aliphatic hydrocarbon ring).

A monovalent hydrocarbon group in which one or more monocyclic rings and one or more polycyclic rings are joined to each other by a single bond may be a group obtained by eliminating one hydrogen group from a monocyclic polycyclic single bond compound. The "monocyclic polycyclic single bond compound" is a compound in which the following are joined by a single bond: one or more of cycloalkane, cycloalkene, cycloalkyne, and compounds in which two or more of cycloalkane, cycloalkene, and cycloalkyne are combined, and one or more of a spiro polycyclic compound, a condensed ring polycyclic compound, a polycyclic hydrocarbon-based polycyclic compound, and compounds in which two or more of these compounds are combined.

A bivalent hydrocarbon group in which one or more monocyclic rings and one or more polycyclic rings are joined to each other by a single bond may be a group obtained by eliminating two hydrogen groups from a monocyclic polycyclic single bond compound.

A trivalent hydrocarbon group in which one or more monocyclic rings and one or more polycyclic rings are joined to each other by a single bond may be a group obtained by eliminating three hydrogen groups from a monocyclic polycyclic single bond compound.

It should be understood that the n-valent hydrocarbon group in which one or more monocyclic rings and one or more polycyclic rings are joined to each other by a single bond may be a tetravalent or higher multivalent hydrocarbon group in which one or more monocyclic rings and one or more polycyclic rings are joined to each other by a single bond The "n-valent group in which one or more monocyclic aliphatic hydrocarbon rings and one or more polycyclic aliphatic hydrocarbon chains are bonded to each other" is an n-valent hydrocarbon group in which one or more monocyclic rings (monocyclic aliphatic hydrocarbon ring) and one or more chained hydrocarbons (aliphatic hydrocarbon chain) are bonded to each other.

The n-valent hydrocarbon group may contain one or two or more monocyclic rings. Likewise, the n-valent hydrocarbon groups may contain one or two or more chained hydrocarbons.

When the number of the monocyclic rings is two or more, the two or more monocyclic rings may be of a single type or two or more different types. Likewise, when the number of the chained hydrocarbons is two or more, the two or more chained hydrocarbons may be of a single type or two or more different types.

The order of bonds that occur between one or more monocyclic rings and one or more chained hydrocarbons is not particularly limited and may optionally follow any sequential order.

In the case of one monocyclic ring and two chained hydrocarbons, for example, a bond may occur in the order of the monocyclic ring, chained hydrocarbon, and chained hydrocarbon, or may occur in the order of chained hydrocarbon, monocyclic ring, and chained hydrocarbon. In the case of two monocyclic rings and two chained hydrocarbons, for example, a bond may occur in any one of the following orders: monocyclic, monocyclic, chained hydrocarbon, and chained hydrocarbon; monocyclic, chained hydrocarbon, monocyclic, and chained hydrocarbon; monocyclic, chained hydrocarbon, chained hydrocarbon, and monocyclic; and chained hydrocarbon, monocyclic, monocyclic, and chained hydrocarbon.

For example, (A) may be referred to for details of the monocyclic ring (monocyclic aliphatic hydrocarbon ring).

The "aliphatic hydrogen chain" is a generic term that refers to chained hydrocarbons each including carbon (C) and hydrogen (H). The aliphatic hydrocarbon chain may be a straight chain or a branched chain having one or two or more side chains. The aliphatic hydrocarbon chain may or may not include one or two or more carbon-carbon unsaturated bonds.

Examples of the aliphatic hydrocarbon chain may include but are not limited to alkyl chain, alkenyl chain, alkynyl chain, and chains in which two or more of the before-mentioned chains are combined (hereinafter, "combined chain").

Examples of the combined chain may include but are not limited to a chain in which alkyl chain and alkenyl chain are combined, a chain in which alkyl chain and alkynyl chain are combined, a chain in which alkenyl chain and alkynyl chain are combined, and a chain in which alkyl chain, alkenyl chain, and alkynyl chain are combined.

Specific examples of the alkyl chain may include methyl chain, ethyl chain, propyl chain, butyl chain, nonyl chain, and decyl chain. Specific examples of the alkenyl chain may include vinyl chain and aryl chain. A specific example of the alkynyl chain may be ethynyl chain. A specific example of the combined chain may be benzyl chain.

A monovalent hydrocarbon group in which one or more monocyclic rings and one or more chained hydrocarbons are bonded to each other may be a group obtained by eliminating one hydrogen group from a monocyclic hydrocarbon chain compound. The "monocyclic hydrocarbon chain compound" is a compound in which the following are combined; one or more of cycloalkane, cycloalkene, cycloalkyne, and compounds in which two or more of cycloalkane, cycloalkene, and cycloalkyne are combined, and one or more of alkyl chain, alkenyl chain, alkynyl chain, and combined chain.

A bivalent hydrocarbon group in which one or more monocyclic rings and one or more chained hydrocarbons are bonded to each other may be a group obtained by eliminating two hydrogen groups from a monocyclic hydrocarbon chain compound.

A trivalent hydrocarbon group in which one or more monocyclic rings and one or more chained hydrocarbons are bonded to each other may be a group obtained by eliminating three hydrogen groups from a monocyclic hydrocarbon chain compound.

It should be understood that the n-valent hydrocarbon group in which one or more monocyclic rings and one or more chained hydrocarbons are bonded to each other may be a tetravalent or higher multivalent hydrocarbon group in which one or more monocyclic rings and one or more chained hydrocarbons are bonded to each other.

The number of carbons in the aliphatic hydrocarbon chain, though not particularly limited, may preferably be between 1 and 12, and more preferably be between 1 and 4. This may provide markedly improved chemical stability of the electrolytic solution, while ensuring solubility and compatibility of the sulfonyl compound.

(Details of (G))

The "n-valent group in which one or more polycyclic aliphatic hydrocarbon rings and one or more aliphatic hydrocarbon chains are bonded to each other" is an n-valent hydrocarbon group in which one or more monocyclic rings (monocyclic aliphatic hydrocarbon ring) and one or more chained hydrocarbons (aliphatic hydrocarbon chain) are bonded to each other.

The n-valent hydrocarbon group may contain one or two or more polycyclic rings. Likewise, the n-valent hydrocarbon groups may contain one or two or more chained hydrocarbons.

Likewise, when the number of the polycyclic rings is two or more, the two or more polycyclic rings may be of a single type or two or more different types. Likewise, when the number of the chained hydrocarbons is two or more, the two or more chained hydrocarbons may be of a single type or two or more different types.

The order of bonds that occur between one or more polycyclic rings and one or more chained hydrocarbons is not particularly limited and may optionally follow any sequential order.

In the case of one polycyclic ring and two chained hydrocarbons, for example, a bond may occur in the order of the polycyclic ring, chained hydrocarbon, and chained hydrocarbon, or may occur in the order of chained hydrocarbon, polycyclic ring, and chained hydrocarbon. In the case of two polycyclic rings and two chained hydrocarbons, for example, a bond may occur in any one of the following orders: polycyclic, polycyclic, chained hydrocarbon, and chained hydrocarbon; polycyclic, chained hydrocarbon, polycyclic, and chained hydrocarbon; polycyclic, chained hydrocarbon, chained hydrocarbon, and polycyclic; and chained hydrocarbon, polycyclic, polycyclic, and chained hydrocarbon.

For example, (B) may be referred to for details of the polycyclic ring (polycyclic aliphatic hydrocarbon ring). For example, (F) may be referred to for details of the chained hydrocarbon (aliphatic hydrocarbon chain).

A monovalent hydrocarbon group in which one or more polycyclic rings and one or more chained hydrocarbons are bonded to each other may be a group obtained by eliminating one hydrogen group from a polycyclic hydrocarbon chain compound. The "polycyclic hydrocarbon chain compound" is a compound in which the following are combined; one or more of a spiro polycyclic compound, a condensed ring polycyclic compound, a polycyclic hydrocarbon-based polycyclic compound, and compounds in which two or more of these compounds are combined, and one or more of alkyl chain, alkenyl chain, alkynyl chain, and combined chain.

A bivalent hydrocarbon group in which one or more polycyclic rings and one or more chained hydrocarbons are bonded to each other may be a group obtained by eliminating two hydrogen groups from a polycyclic hydrocarbon chain compound.

A trivalent hydrocarbon group in which one or more polycyclic rings and one or more chained hydrocarbons are bonded to each other may be a group obtained by eliminating three hydrogen groups from a polycyclic hydrocarbon chain compound.

It should be understood that the n-valent hydrocarbon group in which one or more polycyclic rings and one or more chained hydrocarbons are bonded to each other may be a tetravalent or higher multivalent hydrocarbon group in which one or more monocyclic rings and one or more chained hydrocarbons are bonded to each other.

The "n-valent group in which one or more monocyclic aliphatic hydrocarbon rings, one or more polycyclic aliphatic hydrocarbon rings, and one or more aliphatic hydrocarbon chains are bonded to one another" is an n-valent hydrocarbon group in which one or more monocyclic rings (monocyclic aliphatic hydrocarbon ring), one or more polycyclic rings (polycyclic aliphatic hydrocarbon ring), and one or more aliphatic chained hydrocarbons (aliphatic hydrocarbon chain) are bonded to one another.

The n-valent hydrocarbon group may contain one or two or more monocyclic rings. Likewise, the number of the polycyclic rings included in the n-valent hydrocarbon group may be one or two or more, and the number of the chained hydrocarbons included in the n-valent hydrocarbon group may be one or two or more.

When the number of the monocyclic rings is two or more, the two or more monocyclic rings may be of a single type or two or more different types. When the number of the polycyclic rings is two or more, the two or more polycyclic rings may be of two different types or may be of two or more different types. When the number of the chained hydrocarbons is two or more, the two or more chained hydrocarbons may be of a single type or two or more different types.

The order of bonds that occur among one or more monocyclic rings, one or more polycyclic rings, and one or more chained hydrocarbons is not particularly limited and may optionally follow any sequential order.

In the case of one monocyclic ring, one polycyclic ring, and one chained hydrocarbon, for example, a bond may occur with the monocyclic ring, polycyclic ring, and chained hydrocarbon in this order, may occur with the monocyclic ring, chained hydrocarbon, and polycyclic ring in this order, or may occur with the polycyclic ring, monocyclic ring, and chained hydrocarbon in this order.

For example, (A) may be referred to for details of the monocyclic ring (monocyclic aliphatic hydrocarbon ring). For example, (B) may be referred to for details of the polycyclic ring (polycyclic aliphatic hydrocarbon ring). For example, (F) may be referred to for details of the chained hydrocarbon (aliphatic hydrocarbon chain).

A monovalent hydrocarbon group in which one or more monocyclic rings, one or more polycyclic rings, and one or more chained hydrocarbons are bonded to one another may be a group obtained by eliminating one hydrogen group from a monocyclic polycyclic hydrocarbon chain compound. The "monocyclic polycyclic hydrocarbon chain compound" is a compound in which the following are combined: one or more of cycloalkane, cycloalkene, cycloalkyne, and compounds in which two or more of cycloalkane, cycloalkene, and cycloalkyne are combined; one or more of a spiro polycyclic compound, a condensed ring polycyclic compound, a polycyclic hydrocarbon-based polycyclic compound, and compounds in which two or more of these compounds are combined; and one or more of alkyl chain, alkenyl chain, alkynyl chain, and combined chain.

A bivalent hydrocarbon group in which one or more monocyclic rings, one or more polycyclic rings, and one or more chained hydrocarbons are bonded to one another may be a group obtained by eliminating two hydrogen groups from a monocyclic polycyclic hydrocarbon chain compound.

A trivalent hydrocarbon group in which one or more monocyclic rings, one or more polycyclic rings, and one or more chained hydrocarbons are bonded to one another may be a group obtained by eliminating three hydrogen groups from a monocyclic polycyclic hydrocarbon chain compound.

It should be understood that the n-valent hydrocarbon group in which one or more monocyclic rings, one or more polycyclic rings, and one or more chained hydrocarbons are bonded to one another may be a tetravalent or higher multivalent hydrocarbon group in which one or more monocyclic rings, one or more polycyclic rings, and one or more chained hydrocarbons are bonded to one another.

When the n-valent hydrocarbon group includes one or two or more aliphatic hydrocarbon rings, one or two or more substituent groups, for example, may be introduced into the groups described in A) to H).

Examples of the substituent group may include monovalent aliphatic hydrocarbon groups, and monovalent aromatic hydrocarbon groups. A specific example of the monovalent aliphatic hydrocarbon groups may be a monovalent group in which two or more of alkyl group, alkenyl group, and alkynyl group are boned to each other. The alkyl group, alkenyl group, and alkynyl group will be described later in further detail. A specific example of the monovalent aromatic hydrocarbon groups may be aryl group. Examples of the aryl group may include phenyl group and naphthyl group. When the n-valent hydrocarbon group includes one or two or more aromatic hydrocarbon rings, the n-valent hydrocarbon group may specifically include, for example, one or two or more monovalent aromatic hydrocarbon groups.

The Rf is one of a halogen group and a monovalent halogenated hydrocarbon group.

The n being greater than or equal to 2 means that the sulfonyl compound with two or more branches (—S(=O)$_2$—Rf)) accordingly has two or more Rfs. In this instance, two or more Rfs may be of a single type or two or more different types. The two or more Rfs may be partly of the same type.

Examples of the halogen group may include but are not limited to fluorine group (—F), chlorine group (—Cl), bromine group (—Br), and iodine group (—I). The halogen group may be one selected from any other suitable groups.

Among the examples, the halogen group may preferably be a fluorine group. Such a group may be preferable because it allows the electrolytic solution to further improve in chemical stability.

The "monovalent halogenated hydrocarbon group" is a group obtained by substituting one or two or more hydrogen groups of a monovalent hydrocarbon group with a halogen group(s). As described earlier, the "monovalent hydrocarbon group" is a generic term that refers to monovalent groups each including carbon and hydrogen. The "monovalent hydrocarbon group" may be a straight chain group, a branched group having one or two or more side chains, a cyclic group, or a group in which two or more of the before-mentioned groups are bonded to each other. When the number of the halogen groups is two or more, the two or more halogen groups may be of a single type or two or more different types.

The "monovalent halogenated hydrocarbon group" may or may not include one or two or more carbon-carbon unsaturated bonds. The "monovalent halogenated hydrocarbon group" may have aliphatic properties (non-aromatic properties) or may have aromatic properties.

Examples of the monovalent hydrocarbon group may include but are not limited to alkyl chain, alkenyl chain, alkynyl chain, cycloalkyl group, aryl group, and monovalent groups in which two or more of the before-mentioned groups are bonded to each other (hereinafter, "combined group").

Examples of the combined group may include but are not limited to the following monovalent groups; monovalent group in which the alkyl group and alkenyl group are bonded to each other, monovalent group in which the alkyl group and alkynyl group are bonded to each other, monovalent group in which the alkenyl group and alkynyl group are bonded to each other, monovalent group in which aryl group and cycloalkyl group are bonded to each other, monovalent group in which cycloalkyl group and one or more of alkyl group, alkenyl group, and alkynyl group are bonded to each other, and monovalent group in which aryl group and one or more of alkyl group, alkenyl group, and alkynyl group are bonded to each other.

Specific examples of the alkyl group may include methyl group, ethyl group, propyl group, t-butyl group, nonyl group, and decyl group. Specific examples of the alkenyl group may include vinyl group and aryl group. A specific example of the alkynyl group may be ethynyl group. Examples of the cycloalkyl group may include but are not limited to cyclopropyl group, cyclobutyl group, cyclopentyl group, cyclohexyl group, cycloheptyl group, and cyclooctyl group. Specific examples of the aryl group may include phenyl group and naphthyl group. A specific example of the combined group may be benzyl group.

As mentioned earlier, the halogen group may preferably be a fluorine group, and a preferable example of the monovalent halogenated hydrocarbon group may be accordingly a monovalent fluorinated hydrocarbon group. The "monovalent fluorinated hydrocarbon group is a group obtained by substituting one or two or more hydrogen groups in any one of the before-mentioned monovalent hydrocarbon groups with a fluorine group(s).

Examples of the monovalent fluorinated hydrocarbon group may include but are not limited to fluorinated alkyl group, fluorinated alkenyl group, fluorinated alkynyl group, fluorinated cycloalkyl group, fluorinated aryl group, and monovalent groups in which two or more of the before-mentioned groups are bonded to each other.

Specific examples of the fluorinated alkyl group may include fluoromethyl group, difluoromethyl group, perfluoromethyl group, perfluoroethyl group, perfluoropropyl group, and perfluoro-t-butyl group. A specific example of the fluorinated alkenyl group is perfluorovinyl group. A specific example of the fluorinated cycloalkyl group is perfluorocyclohexyl group. A specific example of the fluorinated aryl group is perfluoroaryl group. A specific example of the fluorinated combined group is perfluorobenzyl group.

Among the examples, the monovalent fluorinated hydrocarbon group may preferably be fluorinated alkyl group, fluorinated alkenyl group, or fluorinated alkynyl group, among which the fluorinated alkyl group may be preferred over the others. A particularly preferable example of the monovalent fluorinated hydrocarbon group is monovalent perfluoroalkyl group. This may provide markedly improved chemical stability of the electrolytic solution, while ensuring solubility and compatibility of the sulfonyl compound.

The number of carbons in the monovalent halogenated hydrocarbon group is not particularly limited. Specifically, the number of carbons in a group obtained by substituting one or two or more hydrogen groups of an alkyl group with a halogen group(s) (halogenated alkyl group) may be, for example, between 1 and 10, and preferably between 1 and 4. A group obtained by substituting one or two or more hydrogen groups with a halogen group(s) in an alkenyl group or alkynyl group (halogenated alkenyl group, halogenated alkynyl group) may contain, for example, 2 to 10 carbons. A group obtained by substituting one or two or more hydrogen groups with a halogen group(s) in a cycloalkyl group or aryl group (halogenated cycloalkyl group, halogenated aryl group) may contain, for example 6 to 18 carbons. This may provide markedly improved chemical stability of the electrolytic solution, while ensuring solubility and compatibility of the sulfonyl compound.

As described earlier, the n is an integer greater than or equal to 1. Thus, the n may unlimitedly take the value of any integer greater than or equal to 1. In accordance with the n value, the valence of the stem (R) is decided, and the number of branches (—S(=O)$_2$—Rf) bonded to the stem is also decided.

Among the possible values, the n may preferably be smaller than or equal to 4. The n may preferably take the value of an integer between 1 and 4. This may provide markedly improved chemical stability of the electrolytic solution, while ensuring solubility and compatibility of the sulfonyl compound.

The sulfonyl compound may preferably include one or both of the compounds expressed by the following Chemical Formulas (2) and (3). This may provide markedly improved chemical stability of the electrolytic solution, while ensuring solubility of the sulfonyl compound.

[Chemical Formula 2]

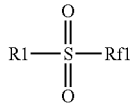
(2)

(where R1 represents a monovalent hydrocarbon group including one or two or more aliphatic hydrocarbon rings, Rf1 is one of a halogen group and a monovalent halogenated hydrocarbon group, and the monovalent hydrocarbon group may include one or two or more aromatic hydrocarbon rings, provided that a ring closest to a sulfur atom forming a sulfonyl group is an aliphatic hydrocarbon ring).

[Chemical Formula 3]

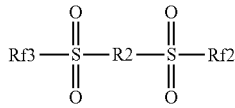
(3)

(where R2 represents a bivalent hydrocarbon group including one or two or more aliphatic hydrocarbon rings, Rf2 and Rf3 are each one of a halogen group and a monovalent halogenated hydrocarbon group, and the bivalent hydrocarbon group may include one or two or more aromatic hydrocarbon rings, provided that a ring closest to a sulfur atom forming a sulfonyl group is an aliphatic hydrocarbon ring).

To distinguish between two types of sulfonyl compounds, the description given below uses "first sulfonyl compound" to refer to the sulfonyl compound expressed by Formula (1), while using "second sulfonyl compound" to refer to the sulfonyl compound expressed by Formula (2). Any compounds which are potential candidates of the sulfonyl compound, for example, the first and second sulfonyl compounds, are collectively referred to as "sulfonyl compound".

The first sulfonyl compound is a compound in which n=1 in Chemical Formula (1), as expressed by Chemical Formula (2). In the first sulfonyl compound, therefore, one branch (—S(=O)$_2$—Rf1) is bonded to the stem (R1).

Details of the R1 (monovalent hydrocarbon group) may be similar to details of the R (n-valent hydrocarbon group) described earlier, except that the valence is limited to monovalence.

Examples of the monovalent hydrocarbon group may include but are not limited to the monovalent groups described in A) to H) and these monovalent groups in which substituent groups are introduced. Specific examples of the monovalent hydrocarbon group may include the following groups.

(A) Group obtained by eliminating one hydrogen group from any one of cycloalkane, cycloalkene, cycloalkyne, and compounds in which two or more of cycloalkane, cycloalkene, and cycloalkyne are combined (for example, cycloalkyl group, cycloalkenyl group, cycloalkynyl group), (B) Group obtained by eliminating two hydrogen groups from any one of a spiro polycyclic compound, a condensation polycyclic compound, a polycyclic hydrocarbon-based polycyclic compound, and compounds in which two or more of these compounds are combined, (C) Group obtained by eliminating one hydrogen group from a single bond monocyclic compound, (D) Group obtained by eliminating one hydrogen group from a single bond polycyclic compound, (E) Group obtained by eliminating one hydrogen group from a monocyclic polycyclic single bond compound, (F) Group obtained by eliminating one hydrogen group from a monocyclic hydrocarbon chain compound, (G) Group obtained by eliminating one hydrogen group from a polycyclic hydrocarbon chain compound, and (H) Group obtained by eliminating one hydrogen group from a monocyclic polycyclic hydrocarbon chain compound.

The monovalent hydrocarbon group may be optional two or more of the before-mentioned groups bonded to each other to become monovalent in whole.

Details of the Rf1 may be similar to the details of Rf described earlier.

The second sulfonyl compound is a compound in which n=2 in Chemical Formula (1), as expressed by Chemical Formula (3). In the second sulfonyl compound, therefore, two branches (—S(=O)$_2$—Rf2 and —S(=O)$_2$—Rf3) are bonded to the stem (R2).

Details of the R2 (bivalent hydrocarbon group) may be similar to details of the R (n-valent hydrocarbon group) described earlier, except that the valence is limited to bivalence.

Examples of the bivalent hydrocarbon group may include but are not limited to the bivalent groups described in A) to H) and these bivalent groups in which substituent groups are introduced. Specific examples of the bivalent hydrocarbon group may include the following groups.

(A) Group obtained by eliminating two hydrogen groups from any one of cycloalkane, cycloalkene, cycloalkyne, and compounds in which two or more of cycloalkane, cycloalkene, and cycloalkyne are combined (for example, cycloalkylene group, cycloalkenylene group, cycloalkynylene group), (B) Group obtained by eliminating two hydrogen groups from any one of a spiro polycyclic compound, a condensation polycyclic compound, a polycyclic hydrocarbon-based polycyclic compound, and compounds in which two or more of these compounds are combined, (C) Group obtained by eliminating two hydrogen groups from a single bond monocyclic compound, (D) Group obtained by eliminating two hydrogen groups from a single bond polycyclic compound, (E) Group obtained by eliminating two hydrogen groups from a monocyclic polycyclic single bond compound, (F) Group obtained by eliminating two hydrogen groups from a monocyclic hydrocarbon chain compound, (G) Group obtained by eliminating two hydrogen groups from a polycyclic hydrocarbon chain compound, and (H) Group obtained by eliminating two hydrogen groups from a monocyclic polycyclic hydrocarbon chain compound.

The bivalent hydrocarbon group may be optional two or more of the groups bonded to each other to become bivalent in whole.

Details of the Rf2 and Rf3 may be similar to details of the Rf described earlier.

Specific examples of the sulfonyl compound are described below. The sulfonyl compound, however, is not necessarily limited to the specific examples given below and may be selected from other compounds.
Examples of the first sulfonyl compound may include the compounds expressed by the following Chemical Formulas (2-1) to (2-20).
[Chemical Formulas (2-1) to (2-20)]
(2-1)
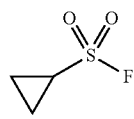
(2-2)
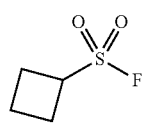
(2-3)
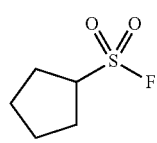
(2-4)
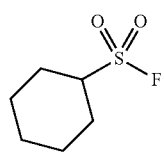
(2-5)
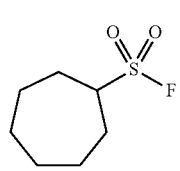
(2-6)
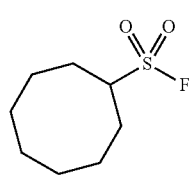
(2-7)
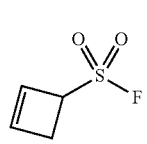
(2-8)
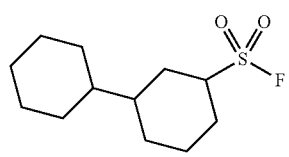
(2-9)
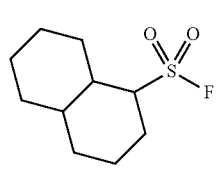
(2-10)
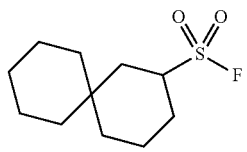
(2-11)
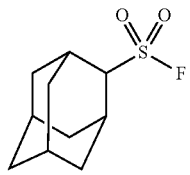
(2-12)
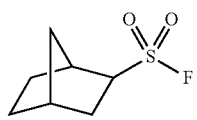
(2-13)
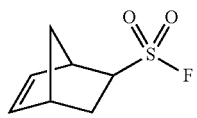
(2-14)
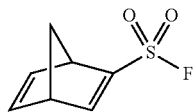
(2-15)
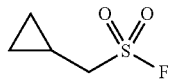
(2-16)
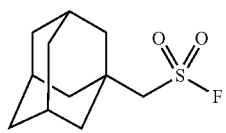
(2-17)
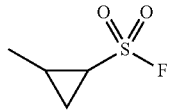
(2-18)
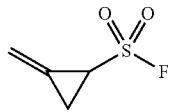
(2-19)
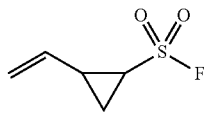
(2-20)
Examples of the second sulfonyl compound may include the compounds expressed by the following Chemical Formulas (3-1) to (3-15).

[Chemical Formula (3-1) to (3-15)]

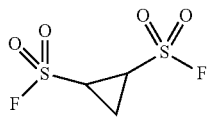 (3-1)

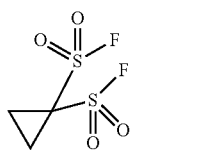 (3-2)

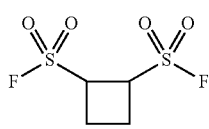 (3-3)

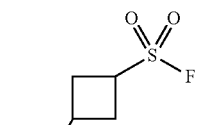 (3-4)

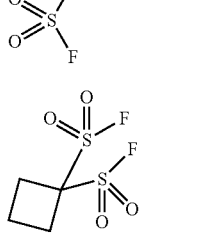 (3-5)

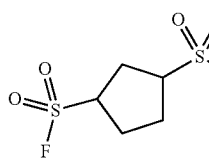 (3-6)

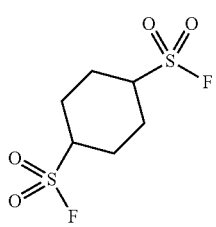 (3-7)

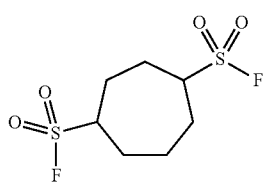 (3-8)

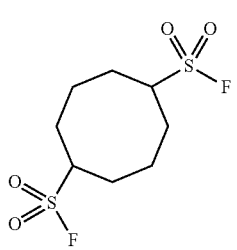 (3-9)

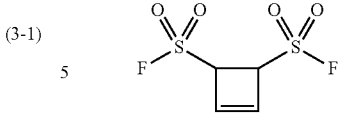 (3-10)

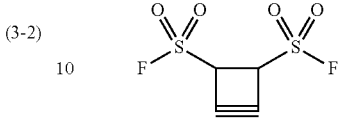 (3-11)

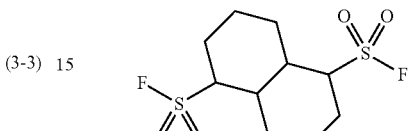 (3-12)

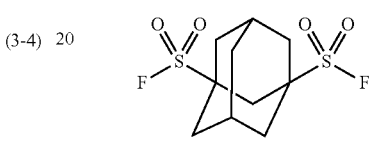 (3-13)

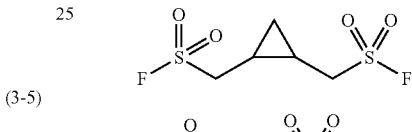 (3-14)

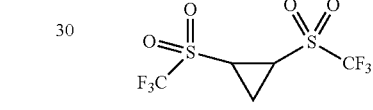 (3-15)

The content of the sulfonyl compound in the electrolytic solution, though not particularly limited, may be between 0.01 wt. % and 5 wt. %. This may provide markedly improved chemical stability of the electrolytic solution, while ensuring solubility and compatibility of the sulfonyl compound.

When the electrolytic solution contains two or more different types of sulfonyl compounds, the "content of the sulfonyl compound" means a summed content of the sulfonyl compounds.

The electrolytic solution contains one or two or more additional materials other than the sulfonyl compound.

Any other additional material may be one or two or more solvents, for example, a non-aqueous solvent(s) (organic solvent). The electrolytic solution containing a non-aqueous solvent(s) is a generally called non-aqueous electrolytic solution.

Examples of the solvent may include cyclic carbonate, chained carbonate, lactone, chained carboxylate, and nitrile (mononitrile). Any one of such solvents may offer outstanding battery capacity, cycle characteristics, and storage characteristics.

Specific examples of the cyclic carbonate may include ethylene carbonate, propylene carbonate, and butylene carbonate. Specific examples of the chained carbonate may include dimethyl carbonate, diethyl carbonate, ethylmethyl carbonate, and methylpropyl carbonate. Specific examples of the lactone may include γ-butyrolactone, and γ-valerolactone. Specific examples of the chained carboxylate may include methyl acetate, ethyl acetate, methyl propionate, ethyl propionate, propyl propionate, methyl butyrate, methyl isobutyrate, methyl trimethylacetate, and ethyl trimethylacetate. Specific examples of the nitrile may include acetonitrile, methoxyacetonitrile, and 3-methoxypropionitrile.

The solvent may include any one(s) selected from, for example, 1,2-dimethoxyethane, tetrahydrofuran, 2-methyltetrahydrofuran, tetrahydropyran, 1,3-dioxolane, 4-methyl-1,3-dioxolane, 1,3-dioxane, 1,4-dioxane, N,N-dimethylformamide, N-methylpyrrolidinone, N-methyloxazolidinone, N,N'-dimethylimidazolidinone, nitromethane, nitroethane, sulfolane, trimethyl phosphate, and dimethyl sulfoxide. These materials may be similarly advantageous.

It may be particularly preferable for the solvent to include any one or two or more selected from ethylene carbonate, propylene carbonate, dimethyl carbonate, diethyl carbonate, and ethylmethyl carbonate. These materials may offer outstanding battery capacity, cycle characteristics, and storage characteristics. In this instance, it may be preferable combine and use the following materials; high-viscosity (high dielectric constant) solvents (for example, relative permittivity $\varepsilon \geq 30$) such as ethylene carbonate and propylene carbonate, and low-viscosity solvents (for example, viscosity $\leq 1$ mPa·s) such as dimethyl carbonate, ethylmethyl carbonate, and diethyl carbonate. These materials may be preferable because they improve detachability of electrolytic salt and mobility of ions.

The solvent may further include any one or two or more selected from unsaturated cyclic carbonate, halogenated carbonate, sulfonate, acid anhydrides, dinitrile compounds, and diisocyanate compounds. These materials may be preferable because they allow the electrolytic solution to further improve in chemical stability.

The unsaturated cyclic carbonate is cyclic carbonate including one or two or more carbon-carbon unsaturated bonds (carbon-carbon double bond), examples of which may include compounds expressed by the following chemical formulas (4) to (6). The content of the unsaturated cyclic carbonate in the solvent, though not particularly limited, may be between 0.01 wt. % and 10 wt. %.

[Chemical Formula (4) to (6)]

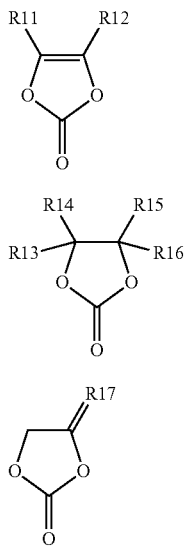

(where R11 and R12 are each one of a hydrogen group and an alkyl group, R13 to R16 are each any one of a hydrogen group, an alkyl group, a vinyl group, and an aryl group, and at least one of R13 to R16 is one of a vinyl group and an aryl group, and R17 is a group expressed by >CR171R172, and R171 and R172 are each one of a hydrogen group and an alkyl group).

The compound expressed by Chemical Formula (4) is a vinylene carbonate-based compound. The groups R11 and R12 may be a single type of or two different types of groups. Details of the alkyl group were described earlier. Examples of the vinylene carbonate-based compound may include vinylene carbonate (1,3-dioxol-2-one), methylvinylene carbonate (4-methyl-1,3-dioxol-2-one), ethylvinylene carbonate (4-ethyl-1,3-dioxol-2-one), 4,5-dimethyl-1,3-dioxol-2-one, 4,5-diethyl-1,3-dioxol-2-one, 4-fluoro-1,3-dioxol-2-one, and 4-trifluoromethyl-1,3-dioxol-2-one.

The compound expressed by Chemical Formula (5) is a vinyl ethylene carbonate-based compound. The groups R13 to R16 may be a single type of or two or more different types of groups. The R13 to R16 may be partly the same type of groups. Examples of the vinyl ethylene carbonate-based compound may include vinyl ethylene carbonate (4-vinyl-1,3-dioxolan-2-one), 4-methyl-4-vinyl-1,3-dioxolan-2-one, 4-ethyl-4-vinyl-1,3-dioxolan-2-one, 4-n-propyl-4-vinyl-1,3-dioxolan-2-one, 5-methyl-4-vinyl-1,3-dioxolan-2-one, 4,4-divinyl-1,3-dioxolan-2-one, and 4,5-divinyl-1,3-dioxolan-2-one.

The compound expressed by Chemical Formula (6) is a methylene ethylene carbonate-based compound. The groups R171 and R172 may be a single type of or two different types of groups. Examples of the methylene ethylene carbonate-based compound may include methylene ethylene carbonate (4-methylene-1,3-dioxolan-2-one), 4,4-dimethyl-5-methylene-1,3-dioxolan-2-one, and 4,4-diethyl-5-methylene-1,3-dioxolan-2-one.

Other than these examples, the unsaturated cyclic carbonate may be catechol carbonate having benzene rings.

The halogenated carbonate is a cyclic or chained carbonate including one or two or more halogens as constituent elements, examples of which may include compounds expressed by the following Chemical Formulas (7) and (8). The content of the halogenated carbonate in the solvent, though not particularly limited, may be between 0.01 wt. % and 10 wt. %.

[Chemical Formulas (7) and (8)]

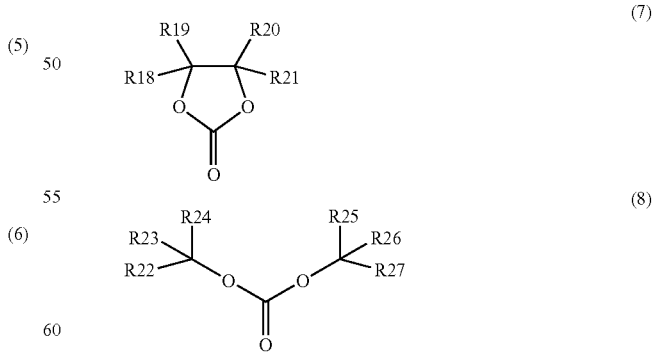

(where R18 to R21 are any one of a hydrogen group, a halogen group, an alkyl group, and a halogenated alkyl group, and at least one of R18 to R21 is one of a halogen group and a halogenated alkyl group, and R22 to R27 are any one of a hydrogen group, a halogen group, an alkyl group, and a halogenated alkyl group, and at least one of R22 to R27 is one of a halogen group and a halogenated alkyl group).

The compound expressed by Chemical Formula (7) is cyclic halogenated carbonate. The groups R18 to R21 may be a single type of or two or more different types of groups. The R18 to R21 may be partly the same type of groups.

The halogen group, though not particularly limited, may preferably be one or two or more selected from a fluorine group, a chlorine group, a bromine group, or an iodine group, among which the iodine group is particularly preferable. The number of halogen groups may be one or two or more.

Details of the alkyl group were described earlier. The "halogenated alkyl group" is a group obtained by substituting one or two or more hydrogen groups of an alkyl group with a halogen group(s) (halogenated). Details of the halogen group were described earlier.

Specific examples of the cyclic halogenated carbonate may include the compounds expressed by the Chemical Formulas (7-1) to (7-21). These compounds include geometrical isomers. Among them, preferable examples may be 4-fluoro-1,3-dioxolan-2-one expressed by Chemical Formula (7-1), and 4,5-difluoro-1,3-dioxolan-2-one expressed by Chemical Formula (7-3). In case 4,5-difluoro-1,3-dioxolan-2-one is used, a trans isomer may be preferred over a cis isomer. The trans isomer may be easily accessible and expected to offer a more powerful effect.

[Chemical Formulas (7-1) to (7-21)]

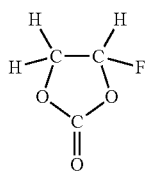

(7-1)

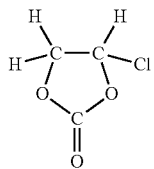

(7-2)

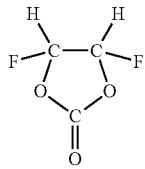

(7-3)

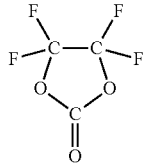

(7-4)

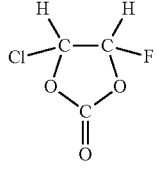

(7-5)

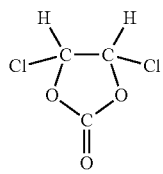

(7-6)

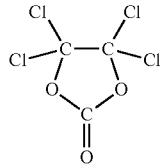

(7-7)

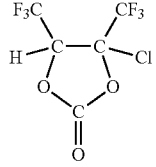

(7-8)

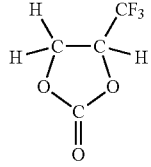

(7-9)

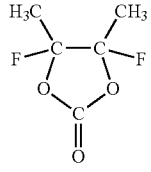

(7-10)

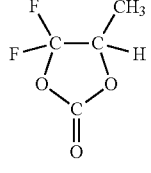

(7-11)

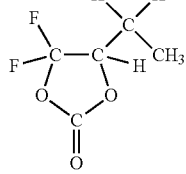

(7-12)

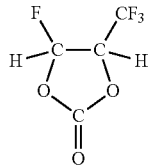

(7-13)

(7-14)

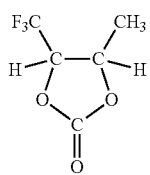
(97-15)

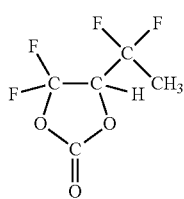
(7-16)

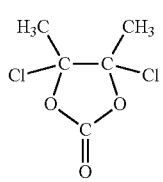
(7-17)

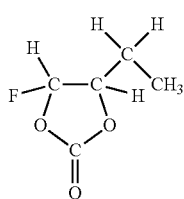
(7-18)

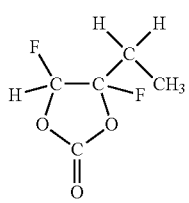
(7-19)

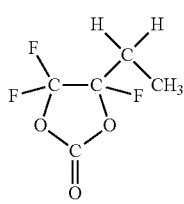
(7-20)

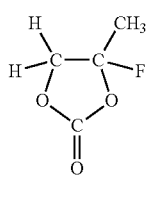
(7-21)

The compound expressed by Chemical Formula (8) is chained halogenated carbonate. The groups R22 to R27 may be a single type of or two or more different types of groups. The R22 to R27 may be partly the same type of groups.

Specific examples of the chained halogenated carbonate may include fluoromethyl methyl carbonate, bis carbonate (fluoromethyl), and difluoromethyl methyl carbonate.

Examples of the sulfonate may include monosulfonate and disulfonate. The content of the sulfonate in the solvent, though not particularly limited, may be between 0.01 wt % and 10 wt %.

The monosulfonate may be one of cyclic monosulfonate and chained monosulfonate. Specific examples of the cyclic monosulfonate may be sultones, for example, 1,3-propansultone and 1,3-propenesultone. Specific examples of the chained monosulfonate may include compounds in which cyclic monosulfonate is broken along the way.

The disulfonate may be one of cyclic disulfonate and chained disulfonate. Examples of the cyclic disulfonate may include the compounds expressed by the Chemical Formulas (9-1) to (9-3). Specific examples of the chained disulfonate may include compounds in which cyclic disulfonate is broken along the way.

[Chemical Formula (9-1) to (9-3)]

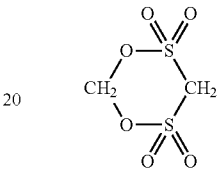
(9-1)

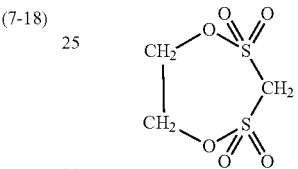
(9-2)

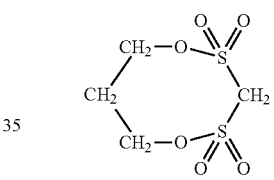
(9-3)

Examples of the acid anhydride may include carboxylic anhydride, disulfonic acid anhydride, and carboxylic-disulfonic acid anhydride. The content of the acid anhydride in the solvent, though not particularly limited, may be between 0.01 wt % and 10 wt %.

Specific examples of the carboxylic anhydride may include succinic anhydride, glutaric acid anhydride, and maleic acid anhydride. Specific examples of the disulfonic acid anhydride may include ethane sulfonic acid anhydride and propane disulfonic acid anhydride. Specific examples of the carboxylic-disulfonic acid anhydride may include sulfobenzoic acid anhydride, sulfopropionic acid anhydride, and sulfobutyric acid anhydride.

The dinitrile compound may be a compound expressed by $NC-C_mH_{2m}-CN$ (where m is an integer greater than or equal to 1). Examples of the dinitrile compound may include succinonitrile ($NC-C_2H_4-CN$), glutaronitrile ($NC-C_3H_6-CN$), adiponitrile ($NC-C_4H_8-CN$), sebaconitrile ($NC-C_8H_{10}-CN$), and phthalonitrile ($NC-C_6H_4-CN$). The content of the dinitrile compound in the solvent, though not particularly limited, may be between 0.5 w to % and 5 wt %.

The diisocyanate compound may be a compound expressed by $OCN-C_nH_{2n}-NCO$ (where n is an integer greater than or equal to 1). The content of the diisocyanate compound in the solvent, though not particularly limited, may be between 0.1 wt % and 10 wt %. A specific example of the diisocyanate compound may be $OCN-C_6H_{12}-NCO$.

Any other additional material may be one or two or more selected from lithium salts and electrolytic salts. The electrolytic salt may include any salt but the lithium salts. Examples of any salt but the lithium salts may include salts of light metals other than lithium.

Specific examples of the lithium salts may include lithium phosphate hexafluoride ($LiPF_6$), lithium tetrafluoride borate ($LiBF_4$), lithium perchlorate ($LiClO_4$), lithium hexafluoride arsenate ($LiAsF_6$), lithium tetraphenylborate ($LiB(C_6H_5)_4$), lithium methane sulfonate ($LiCH_3SO_3$), lithium trifluoromethanesulfonate ($LiCF_3SO_3$), lithium tetrachloroaluminate ($LiAlCl_4$), dilithium hexafluoride silicate ($Li_2SiF_6$), lithium chloride (LiCl), and lithium bromide (LiBr).

The lithium salt may preferably be one or two or more selected from lithium phosphate hexafluoride, lithium tetrafluoride borate, lithium perchlorate, and lithium hexafluoride arsenate, among which lithium phosphate hexafluoride may be particularly preferable. Such lithium salts may favorably lead to a lower internal resistance.

The electrolytic salt may include one or two or more of the compounds expressed by the Chemical Formulas (10) to (12). The groups R41 and R43 may be a single type of or two different types of groups. The groups R51 to R53 may be a single type of or two or more different types of groups. The R51 to R53 may be partly the same type of groups. The groups R61 and R62 may be a single type of or two different types of groups.

[Chemical Formula 10]

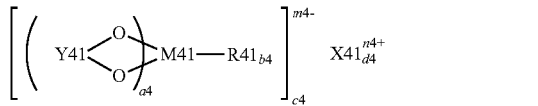

(10)

(where X41 is any one of aluminum (Al) and Group 1 and Group 2 elements of the long-form periodic table, M41 is any one of transition metals and Group 13, Group 14, and Group 15 elements of the long-form periodic table, R41 is a halogen group, Y41 is any one of —C(=O)—R42-C(=O)—, —C(=O)—CR43$_2$-, and C(=O)—C(=O)—, R42 is any one of an alkylene group, a halogenated alkylene group, an arylene group, and a halogenated arylene group, R43 is any one of an alkyl group, a halogenated alkyl group, an aryl group, and a halogenated aryl group, and a4 is an integer from 1 to 4, b4 is an integer selected from 0, 2, and 4, and c4, d4, m4, and n4 are each an integer from 1 to 3).

[Chemical Formula 11]

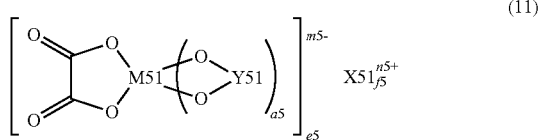

(11)

(where X51 is any one of transition metals and Group 1 and Group 2 elements of the long-form periodic table, M51 is any one of transition metals and Group 13, Group 14, and Group 15 elements of the long-form periodic table, Y51 is any one of —C(=O)—(CR51$_2$)$_{b5}$-C(=O)—, —R53$_2$C—(CR52$_2$)$_{c5}$-C(=O)—, —R53$_2$C—(CR52$_2$)$_{c5}$-CR53$_2$-, —R53$_2$C—(CR52$_2$)$_{c5}$-S(=O)$_2$—, —S(=O)$_2$—(CR52$_2$)$_{d5}$-S(=O)$_2$—, and —C(=O)—(CR52$_2$)$_{d5}$-S(=O)$_2$—, R51 and R53 are any one of a hydrogen group, an alkyl group, a halogen group, and a halogenated alkyl group, at least one of R51 is one of a halogen group and a halogenated alkyl group, and at least one of R53 is one of a halogen group and a halogenated alkyl group, R52 is any one of a hydrogen group, an alkyl group, a halogen group, and a halogenated alkyl group, and a5, e5, and n5 are each an integer from 1 or 2, b5 and d5 are each an integer from 1 to 4, c5 is an integer from 0 to 4, and f5 and m5 are each an integer from 1 to 3).

[Chemical Formula 12]

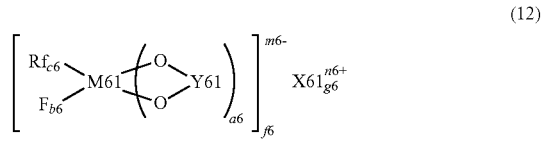

(12)

(where X61 is any one of Group 1 and Group 2 elements of the long-form periodic table, M61 is any one of transition metals and Group 13, Group 14, and Group 15 elements of the long-form periodic table, Rf is one of a fluorinated alkyl group and a fluorinated aryl group, and the fluorinated alkyl group and the fluorinated aryl group respectively contain 1 to 10 carbons, Y61 is any one of, —C(=O)—(CR61$_2$)$_{d6}$-C(=O)—, —R62$_2$C—(CR61$_2$)$_{d6}$-C(=O)—, —R62$_2$C—(CR61$_2$)$_{d6}$-CR62$_2$-, —R62$_2$C—(CR61$_2$)$_{d6}$-S(=O)$_2$—, —S(=O)$_2$—(CR61$_2$)$_{e6}$-S(=O)$_2$—, and —C(=O)—(CR61$_2$)$_{e6}$-S(=O)$_2$—, R61 is any one of a hydrogen group, an alkyl group, a halogen group, and a halogenated alkyl group, R62 is any one of a hydrogen group, an alkyl group, a halogen group, and a halogenated alkyl group, and at least one of R62 is one of a halogen group and a halogenated alkyl group, and a6, f6, and n6 are each an integer from 1 or 2, b6, c6, and e6 are each an integer from 1 to 4, d6 is an integer from 0 to 4, and g6 and m6 area each an integer from 1 to 3).

The Group 1 elements are hydrogen (H), lithium (Li), sodium (Na), potassium (K), rubidium (Rb), cesium (Cs), and francium (Fr). The Group 2 elements are beryllium (Be), magnesium (Mg), calcium (Ca), strontium (Sr), barium (Ba), and radium (Ra). Group 13 elements are boron (B), aluminum (Al), gallium (Ga), indium (In), and thallium (Tl). The Group 14 elements are carbon (C), silicon (Si), germanium (Ge), tin (Sn), and lead (Pb). The Group 15 elements are nitrogen (N), phosphor (P), arsenic (As), antimony (Sb), and bismuth (Bi).

Specific examples of the compound expressed by the following Chemical Formulas (10-1) to (10-6). Specific examples of the compound expressed by the following Chemical Formulas (11-1) to (11-8). A specific examples of the compound expressed by the following Chemical Formula (12-1).

[Chemical Formulas (10-1) to (10-6)]

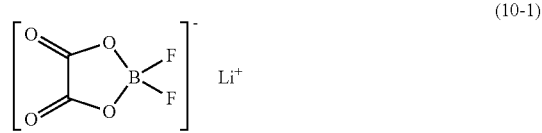

(10-1)

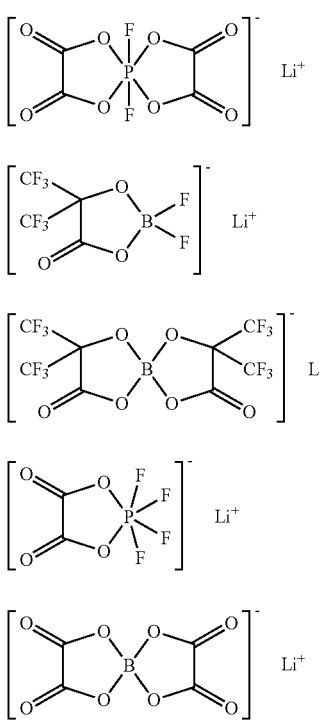

[Chemical Formulas (11-1) to (11-8)]

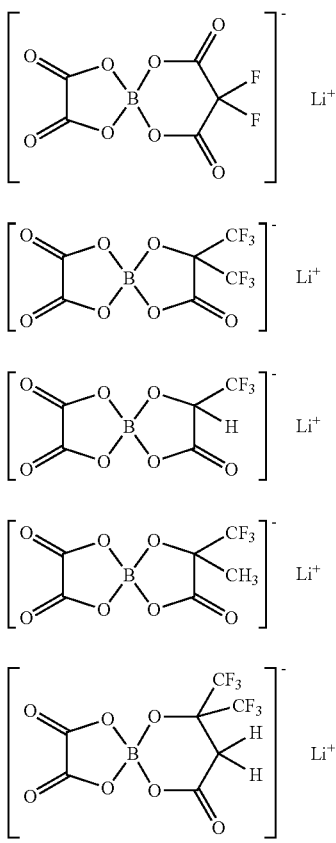

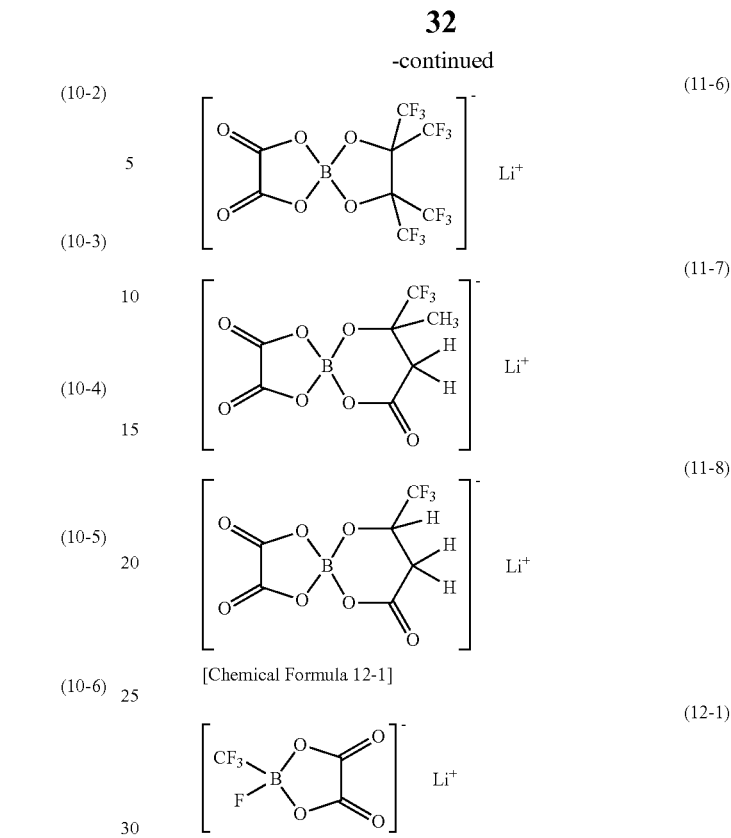

[Chemical Formula 12-1]

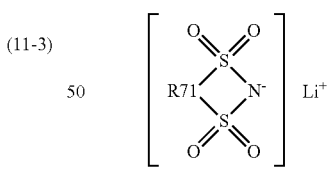

The electrolytic salt may include one or two or more of the compounds expressed by the following Chemical Formulas (13) to (15). In these formulas, m and n may represent an equal value or may represent different values. Further, p, q, and r may represent an equal value or may represent different values. Some of p, q, and r may represent an equal value.

$$\text{LiN}(C_mF_{2m+1}SO_2)(C_nF_{2n+1}SO_2) \tag{13}$$

(where m and n are each an integer greater than or equal to 1).

[Chemical Formula 14]

(where R71 is a straight chain perfluoroalkylene group or a branched perfluoroalkylene group containing 2 to 4 carbons).

$$\text{LiC}(C_pF_{2p+1}SO_2)(C_qF_{2q+1}SO_2)(C_rF_{2r+1}SO_2) \tag{15}$$

(where p, q, and r are each an integer greater than or equal to 1).

The compound expressed by Chemical Formula (13) is a chained imide compound. Specific examples of the chained imide compound may include bis(fluorosulfonyl)imidelithium (LiN(SO$_2$F)$_2$), bis(trifluoromethanesulfonyl)imidelithium (LiN(CF$_3$SO$_2$)$_2$), bis(pentafluoroethanesulfonyl)imidelithium, (LiN(C$_2$F$_5$SO$_2$)$_2$), (trifluoromethanesulfonyl)

(pentafluoroethane sulfonyl)imidelithium (LiN(CF$_3$SO$_2$)(C$_2$F$_5$SO$_2$)), (trifluoromethanesulfonyl)(heptafluoropropanesulfonyl)imidelithium (LiN(CF$_3$SO$_2$)(C$_3$F$_7$SO$_2$)), and (trifluoromethanesulfonyl)(nonafluorobutanesulfonyl)imidelithium (LiN(CF$_3$SO$_2$)(C$_4$F$_9$SO$_2$)).

The compound expressed by Chemical Formula (14) is a cyclic imide compound. Examples of the cyclic imide compound may include the compounds expressed by the following Chemical Formulas (14-1) to (14-4).

[Chemical Formulas (14-1) to (14-4)]

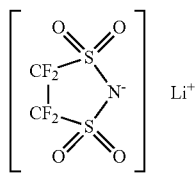

(14-1)

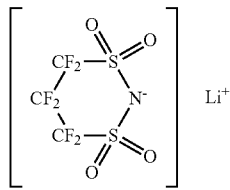

(14-2)

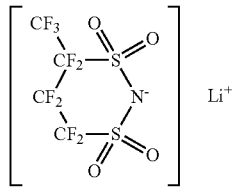

(14-3)

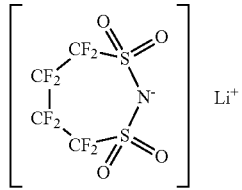

(14-4)

The compound expressed by Chemical Formula (15) is a chained methide compound. A specific example of the chained methide compound may be lithiumtris(trifluoromethanesulfonyl)methide (LiC(CF$_3$SO$_2$)$_3$).

The content of the electrolytic salt, though not particularly limited, may preferably be between 0.3 mol/kg and 3.0 mol/kg relative to the solvent. This may provide remarkable ion conductivity.

Any other one or two or more materials, other than the before-described ones, may be further added. Examples of such additional materials may be phosphorus-fluorine-containing salts including lithium difluorophosphate (LiPF$_2$O$_2$), lithium fluorophosphate (Li$_2$PFO$_3$). The content of the phosphorus-fluorine-containing salt added to the electrolytic solution is not particularly limited.

In an exemplified process to produce the electrolytic solution, an electrolytic salt is added to a solvent, and the resulting solvent is stirred to dissolve or disperse the electrolytic salt in the solvent. Then, a sulfonyl compound is added to the solvent in which the electrolytic salt is dissolved or dispersed, and the resulting solvent is stirred to dissolve or disperse the sulfonyl compound in the solvent. It may be one sulfonyl compound or two or more different sulfonyl compounds that are added to the solvent. As a result, the sulfonyl compound-containing electrolytic solution is obtained.

This electrolytic solution contains the sulfonyl compound described earlier. The sulfonyl compound-containing electrolytic solution may be improved in chemical stability, as compared with a sulfonyl compound-free electrolytic solution or an electrolytic solution containing any other compound. This may inhibit possible decomposition reactions of the electrolytic solution and may reduce the risk of gases being produced from the decomposed electrolytic solution. As a result, properties of a secondary battery using the electrolytic solution may be successfully improved.

The "additional other compound" described earlier is any compound but the sulfonyl compounds, which is more specifically any compound that does to meet the condition expressed by Chemical Formula (1). Examples of such a compound may include the compounds expressed by the following Chemical Formulas (16-1) to (16-11).

[Chemical Formula (16-1) to (16-11)]

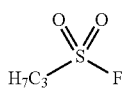

(16-1)

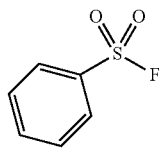

(16-2)

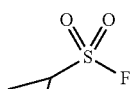

(16-3)

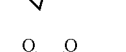

(16-4)

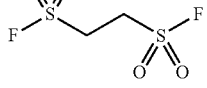

(16-5)

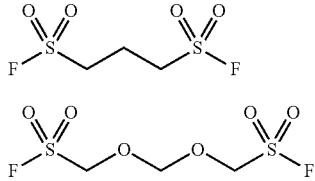

(16-6)

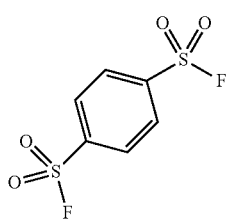

(16-7)

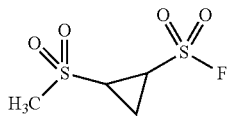

(16-8)

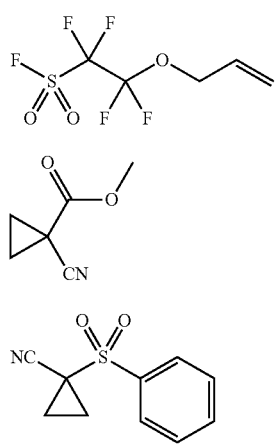

(16-9)

(16-10)

(16-11)

The other compounds expressed by Chemical Formulas (16-1) to (16-3) are added to be compared against the first sulfonyl compound. The other compounds expressed by Chemical Formulas (16-4) to (16-8) are added to be compared against the second sulfonyl compound. The other compounds expressed by Chemical Formulas (16-9) to (16-11) are analogous to the first sulfonyl compound.

The electrolytic solution may be further improved in chemical stability when the n-valent hydrocarbon group does not include one or two or more aromatic hydrocarbon rings, as compared with the n-valent hydrocarbon group including one or two or more aromatic hydrocarbon groups. This may more effectively inhibit decomposition reactions of the electrolytic solution, providing a further improved effect.

The electrolytic solution may be further improved in chemical stability when a sulfur atom is bonded to a carbon atom forming an aliphatic hydrocarbon ring in Chemical Formula (1), as compared with a sulfur atom being bonded a carbon atom irrelevant to the formation of the aliphatic hydrocarbon ring. This may more effectively inhibit decomposition reactions of the electrolytic solution, providing a further improved effect.

The n-valent hydrocarbon group being any one of the n-valent groups listed earlier in (A) to (H) may further improve the electrolytic solution in chemical stability, providing a further improved effect. When the n-valent hydrocarbon group includes one monocyclic aliphatic hydrocarbon ring and the one monocyclic aliphatic hydrocarbon ring contains 3 to 12 or less carbons, the electrolytic solution may even further improve in chemical stability, providing a further improved effect.

When the halogen group is, for example, a fluorine group, and a monovalent halogenated hydrocarbon group is a group obtained by substituting one or two or more hydrogen groups in, for example, an alkyl group with a halogen group(s), the electrolytic solution may even further improve in chemical stability, providing a further improved effect. In this instance, even a better effect may be expected when the number of carbons is 1 to 4 in the monovalent halogenated hydrocarbon group obtained by substituting one or two or more hydrogen groups in an alkyl group with a halogen group(s). The monovalent halogenated hydrocarbon group being a perfluoroalkyl group may further enhance an obtainable effect.

When n is less than or equal to 4, the electrolytic solution may be further improved in chemical stability, leading to a further enhanced effect.

When the sulfonyl compound includes one or both of the first sulfonyl compound expressed by Chemical Formula (2) and the second sulfonyl compound expressed by Chemical Formula (3), the electrolytic solution may be further improved in chemical stability, leading to a further enhanced effect.

The content of 0.01 wt % to 5 wt % of the sulfonyl compound in the electrolytic solution may even further improve the electrolytic solution in chemical stability, providing an even better effect.

Next, a secondary battery using the electrolytic solution according to the technology disclosed herein is hereinafter described.

Figure 2:
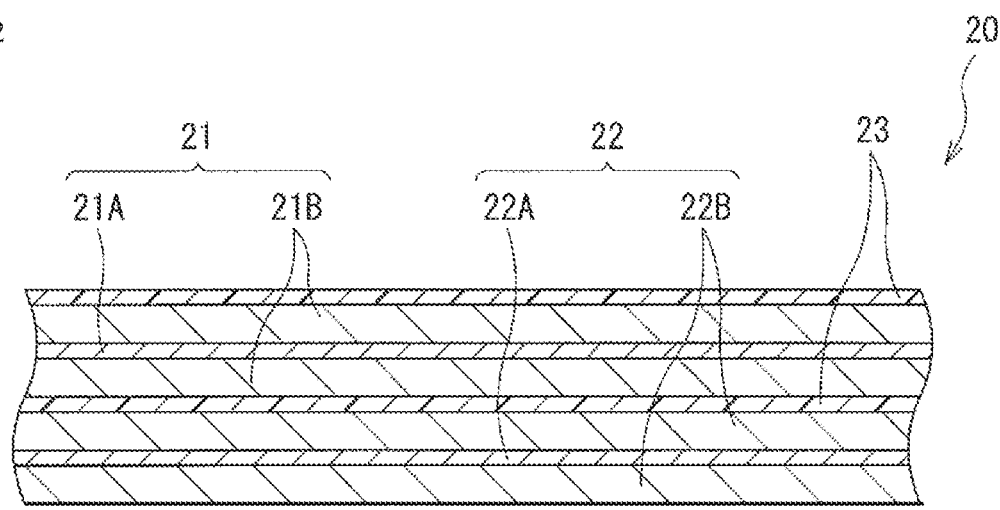
FIG. 2 is an enlarged cross-sectional view in part of a rolled electrode illustrated in FIG. 1.

FIG. 1 is a cross-sectional view of the secondary battery. FIG. 2 is a cross-sectional view in part of a rolled electrode 20 illustrated in FIG. 1.

This secondary battery described herein may be a lithium ion secondary battery, in which the capacity of a negative electrode 22 is acquired by insertion and extraction of an electrode reaction material, lithium.

This secondary battery has a generally cylindrical structure. In this battery, a pair of insulating plates 12 and 13 and a rolled electrode 20 as cell element are housed in a hollow, columnar battery can 11, as illustrated in FIG. 1. The rolled electrode 20 is so structured that a positive electrode 21 and a negative electrode 22 are stacked in layers with a separator 23 interposed therebetween, and the positive electrode 21, negative electrode 22, and separator 23 are all together wound in a roll. The rolled electrode 20 is impregnated with an electrolytic solution which is an electrolyte prepared in liquid form.

The battery can 11 has a hollow structure with a closed end on one end and an opening end on the other side. The battery can 11 may be made of a material(s) including, for example, one or two or more selected from iron, aluminum, and an alloy of these metals. The surface of the battery can 11 may be plated with, for example, nickel. The insulating plates 12 and 13 provided in a pair are disposed at positions across the rolled electrode 20 perpendicularly to its rolled surface.

At the opening end of the battery can 11 are crimped a battery lid 14, a safety valve mechanism 15, and a thermally sensitive resistor (PTC element) 16 with a gasket 17 interposed therebetween. Thus, the battery can 11 is air-tightly sealed. The battery lid 14 may be made of a material(s) similar to that of the battery can 11. The safety valve mechanism 15 and the thermally sensitive resistor 16 are both disposed at positions on the inner side of the battery lid 14. The safety valve mechanism 15 is electrically connected to the battery lid 14 through the thermally sensitive resistor 16. In the safety valve mechanism 15, a disc plate 15A is reversed when the internal pressure of the battery reaches or surpasses a certain level as result of internal short circuit or under heat transmitted from outside. This disrupts electrical connection between the battery lid 14 and the rolled electrode 20. To prevent excessive heat resulting from large current, the resistance of the thermally sensitive resistor 16 increases with a temperature rise. The sealing gasket 17 may be made of an insulating material and may have an asphalt-coated surface.

A center pin 24, for example, is inserted through the rolled electrode 20 at its center. The position at which the center pin 24 is inserted through, however, is not necessarily limited to the center of the rolled electrode 20. A positive electrode lead 25 is attached to the positive electrode 21, and a negative electrode lead 26 is attached to the negative electrode 22. The positive electrode lead 25 may include a conductive material, an example of which is aluminum. The positive electrode lead 25 may be attached to the safety valve mechanism 15 and electrically connected to the battery lid 14. The negative electrode lead 26 may include a conductive material, an example of which is nickel. The negative electrode lead 26 may be attached to and electrically connected to the battery can 11.

As illustrated in FIG. 2, the positive electrode 21 includes, for example, a positive electrode current collector 21A and positive electrode active material layers 21B formed on both surfaces of the positive electrode current collector 21A. The positive electrode active material layer 21B, however, may be formed on one surface alone of the positive electrode current collector 21A.

The positive electrode current collector 21A includes, for example, one or two or more different conductive materials. Examples of the conductive material may include but are not limited to metal materials including aluminum, nickel, and stainless steel. The positive electrode current collector 21A may solely consist of one layer or may have a multilayered structure.

The positive electrode active material layer 21B includes, as an active material for positive electrode, one or two or more different positive electrode materials that can insert and extract lithium. The positive electrode active material layer 21B may further include one or two or more different other materials, for example, positive electrode binder and/or positive electrode conductive material.

The positive electrode material may preferably be a lithium-containing compound. Specifically, the positive electrode material may preferably be one of or both of a lithium-containing composite oxide and a lithium-containing phosphate compound. Such a compound may enable higher energy density.

The lithium-containing composite oxide is an oxide containing lithium and one or two or more other elements (any elements but lithium) as constituent materials. This oxide may have a layered rock-salt crystalline structure or a spinel-type crystalline structure. The lithium-containing phosphate compound is a phosphate compound containing lithium and one or two or more other elements as constituent materials. This compound may have an olivine-type crystalline structure.

The other element(s) is not particularly limited insofar as one or two or more of optional elements are used. Among the possible candidates, the other element(s) may be one or two or more different ones of Group 2 to Group 15 elements of the long-form periodic table. Specifically, preferable examples of the other element(s) may include one or two or more metal elements selected from nickel (Ni), cobalt (Co), manganese (Mn), and iron (Fe). Such a metal element may enable high voltages.

Examples of the lithium-containing composite oxide having a layered rock-salt crystalline structure may include the compounds expressed by the following Chemical Formulas (21) to (23).

$$Li_aMn_{(1-b-c)}Ni_bM11_cO_{(2-d)}F_e \quad (21)$$

(where, M11 is at least one selected from cobalt (Co), magnesium (Mg), aluminum (Al), boron (B), titanium (Ti), vanadium (V), chrome (Cr), iron (Fe), copper (Cu), zinc (Zn), zirconium (Zr), molybdenum (Mo), tin (Sn), calcium (Ca), strontium (Sr), and tungsten (W), a to e have values that satisfy $0.8 \le a \le 1.2$, $0 < b < 0.5$, $0 \le c \le 0.5$, $(b+c) < 1$, $-0.1 \le d \le 0.2$, and $0 \le e \le 0.1$, and the composition of lithium differs with a degree of charge and discharge, where a represents a value at full discharge).

$$Li_aNi_{(1-b)}M12_bO_{(2-c)}F_d \quad (22)$$

(where M12 is at least one selected from cobalt (Co), manganese (Mn), magnesium (Mg), aluminum (Al), boron (B), titanium (Ti), vanadium (V), chrome (Cr), iron (Fe), copper (Cu), zinc (Zn), molybdenum (Mo), tin (Sn), calcium (Ca), strontium (Sr), and tungsten (W), a to d have values that satisfy $0.8 \le a \le 1.2$, $0.005 \le b \le 5$ $0.5$, $-0.1 \le c \le 0.2$, and $0 \le d \le 0.1$, and the composition of lithium differs with a degree of charge and discharge, where a represents a value at full discharge).

$$Li_aCo_{(1-b)}M13_bO_{(2-c)}F_d \quad (23)$$

(where M13 is at least one selected from nickel (Ni), manganese (Mn), magnesium (Mg), aluminum (Al), boron (B), titanium (Ti), vanadium (V), chrome (Cr), iron (Fe), copper (Cu), zinc (Zn), molybdenum (Mo), tin (Sn), calcium (Ca), strontium (Sr), and tungsten (W), a to d have values that satisfy $0.8 \le a \le 1.2$, $0 \le b < 0.5$, $-0.1 \le c \le 0.2$, and $0 \le d \le 0.1$, and the composition of lithium differs with a degree of charge and discharge, where a represents a value at full discharge).

Specific examples of the lithium-containing composite oxide having a layered rock-salt crystalline structure may include $LiNiO_2$, $LiCoO_2$, $LiCo_{0.98}Al_{0.01}Mg_{0.01}O_2$, $LiNi_{0.5}Co_{0.2}Mn_{0.3}O_2$, $LiNi_{0.8}Co_{0.15}Al_{0.05}O_2$, $LiNi_{0.33}Co_{0.33}Mn_{0.33}O_2$, $Li_{1.2}Mn_{0.52}Co_{0.175}Ni_{0.1}O_2$, and $Li_{1.15}(Mn_{0.65}Ni_{0.22}Co_{0.13})O_2$.

When the lithium-containing composite oxide having a layered rock-salt crystalline structure contains, as constituents materials, nickel, cobalt, manganese, and aluminum, the ratio of nickel atoms in this oxide may preferably be 50 at % or more. Such a compound may enable higher energy density.

An example of the lithium-containing composite oxide having a spinel-type crystalline structure may be the compound expressed by the following Chemical Formula (24).

$$Li_aMn_{(2-b)}M14_bO_cF_d \quad (24)$$

(where M14 is at least one selected from cobalt (Co), nickel (Ni), magnesium (Mg), aluminum (Al), boron (B), titanium (Ti), vanadium (V), chrome (Cr), iron (Fe), copper (Cu), zinc (Zn), molybdenum (Mo), tin (Sn), calcium (Ca), strontium (Sr), and tungsten (W), a to d have values that satisfy $0.9 \le a \le 1.1$, $0 \le b \le 0.6$, $3.7 \le c \le 4.1$, and $0 \le d \le 0.1$, and the composition of lithium differs with a degree of charge and discharge, where a represents a value at full discharge).

A specific example of the lithium-containing composite oxide having a spinel-type crystalline structure may be $LiMn_2O_4$.

An example of the lithium-containing phosphate compound having an olivine-type crystalline structure may be the compound expressed by the following Chemical Formula (25).

$$Li_aM15PO_4 \quad (25)$$

(where M15 is at least one selected from cobalt (Co), manganese (Mn), iron (Fe), nickel (Ni), magnesium (Mg), aluminum (Al), boron (B), titanium (Ti), vanadium (V), niobium (Nb), copper (Cu), zinc (Zn), molybdenum (Mo), calcium (Ca), strontium (Sr), tungsten (W), and zirconium (Zr), a has a value that satisfies $0.9 \le a \le 1.1$, and the composition of lithium differs with a degree of charge and discharge, where a represents a value at full discharge).

Specific examples of the lithium-containing phosphate compound having an olivine-type crystalline structure may include $LiFePO_4$, $LiMnPO_4$, $LiFe_{0.5}Mn_{0.5}PO_4$, and $LiFe_{0.3}Mn_{0.7}PO_4$.

Another example of the lithium-containing composite oxide may be the compound expressed by the following Chemical Formula (26).

$$(Li_2MnO_3)_x(LiMnO_2)_{1-x} \qquad (26)$$

(where x has a value that satisfies $0 \leq x \leq 1$, and the composition of lithium differs with a degree of charge and discharge, where x represents a value at full discharge).

Other examples of the positive electrode material may be one or two or more selected from oxides, disulfides, chalcogenides, and conductive high molecular materials. Examples of the oxides may include titanium oxide, vanadium oxide, and manganese dioxide. Examples of the disulfides may include titanium disulfide and molybdenum sulfide. An example of the chalcogenides may be niobium selenide. Examples of the conductive high molecular materials may include sulfur, polyaniline, and polythiophene. The positive electrode material, however, may be selected from any other suitable materials.

The positive electrode binder may include one or two or more selected from synthetic rubbers and high molecular compounds. Examples of the synthetic rubbers may include styrenebutadiene-based rubbers, fluorine-based rubbers, and ethylene propylene diene. Examples of the high molecular compounds may include polyvinylidene fluoride and polyimide.

The positive electrode conductive material includes, for example, one or two or more carbon materials. Examples of the carbon materials may include graphite, carbon black, and Ketjen black. The positive electrode conductive material, however, may be selected from any metal materials and conductive high molecular materials having conductivity.

As illustrated in FIG. 2, the negative electrode 22 includes, for example, a negative electrode current collector 22A and negative electrode active material layers 22B formed on both surfaces of the negative electrode current collector 22A. The negative electrode active material layer 22B, however, may be formed on one surface alone of the negative electrode current collector 22A.

The negative electrode current collector 22A includes, for example, one or two or more different conductive materials. Examples of the conductive material may include but are not limited to metal materials including copper, aluminum, nickel, and stainless steel. The negative electrode current collector 22A may solely consist of one layer or may have a multilayered structure.

The negative electrode current collector 22A may preferably have roughened surfaces. This may provide a generally called anchor effect, which ensures closer contact of the negative electrode active material layers 22B with the negative electrode current collector 22A. Such an effect may be obtainable insofar as the surface of the negative electrode current collector 22A is roughened in at least its region facing the negative electrode active material layers 22B. The surface roughening treatment employed then is, for example, formation of fine grains through electrolysis. By subjecting the negative electrode current collector 22A to electrolysis in an electrolysis vessel, fine grains are formed on the surfaces of the negative electrode current collector 22A, which roughens the surfaces. A copper foil produced by electrolysis is conventionally called an electrolytic copper foil.

The negative electrode active material layer 22B includes, as an active material for negative electrode, one or two or more different negative electrode materials that can insert and extract lithium. The negative electrode active material layer 22B may further include one or two or more different other materials, for example, negative electrode binder and/or negative electrode conductive agent.

The maximum capacity for charge of the negative electrode material may preferably be greater than the discharge capacity of the positive electrode 21 so as to prevent lithium metal from being accidentally deposited on the negative electrode 22 during the battery charge. In other words, the electrochemical equivalent of the negative electrode material that can insert and extracts lithium may preferably be greater than that of the positive electrode 21.

The negative electrode material may be, for example, one or two or more different carbon materials. This may allow higher energy density because of few changes in crystalline structure during lithium insertion and extraction. The carbon material that functions as a negative electrode conductive agent as well may improve the conductivity of the negative electrode active material layer 22B.

Examples of the carbon material may include easily graphitizable carbons, non-graphitizing carbons, and graphite. In the case of non-graphitizing carbon, spacing between (002) planes may preferably 0.37 nm or more. In the case of graphite, spacing between (002) planes may preferably be 0.34 nm or less. Specific examples of the carbon materials may include pyrolytic carbons, cokes, glassy carbon fibers, fired materials of organic high molecular compounds, activated carbons, and carbon blacks. Among these examples, the cokes may include pitch coke, needle coke, and petroleum coke. The fired materials of organic high molecular compounds may refer to high molecular materials including phenol resin and furan resin that are fired (carbonated) at appropriate temperatures. The carbon material may be selected from amorphous carbons and low-crystalline carbons thermally treated at temperatures of approximately 1,000° C. or less. The carbon material may be prepared in various forms, for example, fibrous, spherical, granular, or scaly.

The negative electrode material may be a material including, as its constituent material, one or two or more different metal elements and semi-metal elements (metal-based material). Such materials may enable higher energy density.

The metal-based material may be any one of a simple metal material, an alloy, a compound, a mixture of two or more of these materials, and a material containing in at least part one or two or more phases of these materials. The alloy includes, in addition to a material containing two or more different metal elements, a material containing one or more metal elements and one or more semi-metal elements. The alloy, however, may contain a non-metal element(s). The before-mentioned metal-based materials may be prepared in the form of a solid solution, eutectic (eutectic mixture), an intermetallic compound, or a mixture of two or more of them.

The metal element and the semi-metal element may be one or two or more selected from metal elements and semi-metal elements that can form alloys with lithium. Specific examples may include magnesium (Mg), boron (B), aluminum (Al), gallium (Ga), indium (In), silicon (Si), germanium (Ge), tin (Sn), lead (Pb), bismuth (Bi), cadmium (Cd), silver (Ag), zinc, hafnium (Hf), zirconium, yttrium (Y), palladium (Pd), and platinum (Pt).

Among these examples, one or both of silicon and tin may preferably be used. These materials may be particularly preferable because they excel in lithium insertion-extraction ability and accordingly allow remarkably high energy density to be obtained.

The material containing, as its constituent material, one or both of silicon and tin may be any one of a simple substance of silicon, an alloy, a compound, and/or a simple substance of tin, an alloy, and a compound, or may be two or more of these materials or a material containing at least in part one or two or more phases of these materials. The simple substance described herein does not necessarily indicate 100% purity but should be construed the same as what is conventionally termed (a trace amount of impurity possibly included).

The silicon-based alloy may include, as constituent material other than silicon, any one or two or more selected from tin, nickel, copper, iron, cobalt, manganese, zinc, indium, silver, titanium germanium, bismuth, antimony, and chrome. The silicon-containing compound may include, as constituent material other than silicon, one or two or more of substances including carbon and oxygen. The silicon-containing compound may include, as constituent material other than silicon, one or two or more selected from the substances described in relation to the silicon-based alloy.

Examples of the silicon-based alloy and the silicon-containing compound may include $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_3Si$, $FeSi_2$, $MnSi_2$, $NbSi_2$, $TaSi_2$, $VSi_2$, $WSi_2$, $ZnSi_2$, $SiC$, $Si_3N_4$, $Si_2N_2O$, $SiO_v(0<v\leq2)$, and $LiSiO$. v in $SiO_v$ may be in the range of $0.2<v<1.4$.

The tin-based alloy may include, as constituent material other than tin, any one or two or more selected from silicon, nickel, copper, iron, cobalt, manganese, zinc, indium, silver, titanium, germanium, bismuth, antimony, and chrome. The tin-containing compound may include, as constituent material other than tin, one or two or more of substances including carbon and oxygen. The tin-containing compound may include, as constituent material other than tin, one or two or more selected from the substances described in relation to the tin-based alloy.

Specific examples of the tin-based alloy and the tin-containing compound may include $SnO_w(0<w\leq2)$, $SnSiO_3$, $LiSnO$, and $Mg_2Sn$.

The material containing tin as constituent material may preferably be a material containing tin as a first constituent material and further containing second and third constituent materials (Sn-containing material). Examples of the second constituent material may include one or two or more selected from cobalt, iron, magnesium, titanium, vanadium, chrome, manganese, nickel, copper, zinc, gallium, zirconium, niobium, molybdenum, silver, indium, cesium (Ce), hafnium (Hf), tantalum, tungsten, bismuth, and silicon. The third constituent material may include one or two or more selected from boron, carbon, aluminum, and phosphor. The Sn-containing material further including the second and third constituents may successfully offer remarkable battery capacity and outstanding cycle characteristics.

Among the examples, the Sn-containing material may preferably be a material containing, as constituent materials, tin, cobalt, and carbon (SnCoC-containing material). In the SnCoC-containing material, the content of carbon may be 9.9 mass % to 29.7 mass %, and the ratio of tin-cobalt content (Co/(Sn+Co)) may be 20 mass % to 70 mass %. Such materials may enable higher energy density.

Preferably, the SnCoC-containing material has a phase including tin, cobalt, and carbon, and the phase is a low-crystalline or amorphous phase. This phase is a reaction phase that can react with lithium. The presence of such a phase may provide remarkable properties. The half-value width (diffraction angle of 2θ) of a diffraction peak obtained by X-ray diffraction of this reaction phase may preferably be 1° or more when CuKα ray is used as a specific X ray and 1°/min is set as an intercalation/elimination rate. This may allow more smooth insertion and extraction of lithium and may weaken reactivity with the electrolytic solution. The SnCoC-containing material may possibly include, in addition to the low-crystalline or amorphous phase, a phase including simple substances of constituent materials in whole or in part.

Whether the diffraction peak obtained by X-ray diffraction corresponds to the reaction phase that can react with lithium may be easily determined by comparison between X-ray diffraction charts obtained before and after electrochemical reactions with lithium. When the diffraction peak changes its position before and after the electrochemical reactions with lithium, the diffraction peak is known to correspond to the reaction phase that can react with lithium. In this instance, the diffraction peak of the low-crystalline or amorphous reaction phase may be observed in the range of 2θ=20° to 50°. Such a reaction phase may include the constituent materials described above, and its low-crystalline or amorphous state may be attributable to carbon being present.

In the SnCoC-containing material, a constituent, carbon, may preferably be bonded at least in part to the other constituent; metal element or semi-metal element. This may suppress the degree of aggregation or crystallization of tin. The degree of bonding between the elements may be checked by X-ray photoelectron spectroscopy (XPS). In commercially available devices, for example, Al—Kα ray or Mg—Kα ray may be used as soft X-ray. When carbon is bonded at least in part to the metal element or semi-metal element, for example, the composite wave peak of 1s orbital (C1s) of carbon may appear in a range below 284.5 eV. The apparatus may be energy-calibrated so as to obtain the 4f orbital peak of a gold atom (Au4f) at 84.0 eV. Due to the fact that the surface may typically have surface-contaminating carbon, the C1s peak of the surface-contaminating carbon is set to 284.8 eV, which is used as an energy reference. In the XPS measurement, the C1s peak waveform may take a form including peaks of the surface-contaminating carbon and of carbon in the SnCoC-containing material. The waveform, therefore, may be analyzed with a commercially available software to separate these peaks. To analyze the waveform, the position of a main peak present in the vicinity of a minimum binding energy is defined as the energy reference (284.8 eV).

The SnCoC-containing material is not necessarily limited to materials solely consisting of tin, cobalt, and carbon (SnCoC). Preferable examples of the SnCoC-containing material may include, in addition to tin, cobalt, and carbon, one or two or more selected from silicon, iron, nickel, chrome, indium, niobium, germanium, titanium, molybdenum, aluminum, phosphor, gallium, and bismuth.

Other than the SnCoC-containing material, a material containing, as constituent materials, tin, cobalt, and carbon (SnCoFeC-containing material) may also be preferable. The SnCoFeC-containing material may have an optional composition. When the content of iron is desirably reduced, for example, the content of carbon may be 9.9 mass % to 29.7 mass %, the content of iron may be 0.3 mass % to 5.9 mass %, and the ratio of tin-cobalt content (Co/(Sn+Co)) may be 30 mass % to 70 mass %. When the content of iron is desirably increased, the content of carbon may be 11.9 mass % to 29.7 mass %, the ratio of tin-cobalt-iron content ((Co+Fe)/(Sn+Co+Fe)) may be 26.4 mass % to 48.5 mass %, and the ratio of cobalt-iron content (Co/(Co+Fe)) may be 9.9 mass % to 79.5 mass %. These compositional ranges may provide higher energy density. The physical properties of the SnCoFeC-containing material (for example, half-value width) may be similar to those of the SnCoC-containing material.

Other examples of the negative electrode material may be one or two or more selected from metal oxides and high molecular compounds. Examples of the metal oxides may include iron oxide, ruthenium oxide, and molybdenum oxide. Examples of the high molecular compounds may include polyacetylene, polyaniline, and polypyrrole.

Among the examples, the negative electrode material may preferably include both of a carbon material and a metal-based material because of the following reasons.

A high theoretical capacity may be an advantage with any material containing, as constituent material, a metal-based material, particularly one or both of silicon and tin. Such a material, however, may have an issue; intensive expansion and contraction during the battery charge and discharge. On the other hand, carbon materials characterized by low theoretical capacity may be unlikely to expand or contract during the battery charge and discharge. Therefore, combined use of a carbon material and a metal-based material may allow a high theoretical capacity (i.e., battery capacity) to be achieved, while suppressing possible expansion and contraction during the battery charge and discharge.

The negative electrode active material layer 22B may be formed by one or two or more different techniques selected from coating, gas phase growth, liquid phase growth, flame spraying, and firing (sintering). The coating technique mixes grains (powder) of the negative electrode active material with, for example, a negative electrode binder and disperses the mixture in an organic solvent, and then coats the negative electrode current collector 22A with the mixture-dispersed organic solvent. Examples of the gas phase growth technique may include physical deposition and chemical deposition. Specific examples may include vacuum evaporation, sputtering, ion plating, laser ablation, thermochemical gas phase growth, chemical gas phase growth (CVD), and plasma chemical gas phase growth. Examples of the liquid phase growth may include electrolytic plating and electroless plating. The flame spraying technique sprays a molten or semi-molten negative electrode active material against the negative electrode current collector 22A. In the firing technique, for example, the negative electrode current collector 22A coated with the mixture-dispersed organic solvent by the coating technique is heated at higher temperatures than the melting point of the negative electrode binder. Examples of the firing technique may include atmosphere firing, reaction firing, and hot-press firing.

In the secondary battery described herein, the electrochemical equivalent of the negative electrode material that can insert and extract lithium is greater than that of the positive electrode, as described earlier, in order to prevent lithium from being accidentally deposited on the negative electrode 22 during the battery charge. When an open circuit voltage at full charge (i.e., battery voltage) is 4.25 V or more, for example, the amount of extracted lithium per unit mass may increase, even with the same positive electrode active material, as compared with the open circuit voltage of 4.20 V. The amounts of the positive electrode active material and the negative electrode active material are, therefore, adjusted to deal with this issue. This may provide higher energy density.

As illustrated in FIG. 2, the separator 23 may be interposed between the positive electrode 21 and the negative electrode 22. The separator 23 serves to separate the positive electrode 21 and the negative electrode 22 from each other and allows passage of lithium ions, avoiding possible short circuit of electric current due to contact between these electrodes.

The separator 23 may be a porous film made of, for example, one or two or more of materials including synthetic resins and ceramic or may be a multilayered film including two or more porous films respectively made of, for example, two or more of such materials. Examples of the synthetic resin may include polytetrafluoroethylene, polypropylene, and polyethylene.

The separator 23 may include the porous film (base layer) described above and a high molecular compound layer(s) formed on one of or both of surfaces of the base layer. Then, improved adhesion may be obtained between the separator 23 and the positive and negative electrodes 21 and 22, and the risk of possible distortion of the rolled electrode 20 may be suppressed. This may inhibit decomposition reactions of the electrolytic solution and reduce the risk of leakage of the electrolytic solution from the base layer. As a result, repeated charge and discharge may be less likely to increase the battery resistance, and the degree of swelling of the battery may be suppressed.

The high molecular compound layer includes a high molecular compound, for example, polyvinylidene fluoride. Such a compound may provide physical strength and electrochemical stability. The high molecular compound, however, is not necessarily limited to polyvinylidene fluoride. To form the high molecular compound layer, for example, the high molecular compound is dissolved in an organic solvent to prepare a compound-containing solution, and the prepared solution is applied to the base layer and then dried. Instead, the base layer may be immersed in the solution and then dried. The high molecular compound layer may include a single type of or two or more different types of insulating grains such as inorganic grains. Examples of the inorganic grains may include grains of aluminum oxide and of aluminum nitride.

As described earlier, the rolled electrode 20 is impregnated with an electrolytic solution. This electrolytic solution is similar in composition to the electrolytic solution according to the technology disclosed herein. As such, the electrolytic solution includes a sulfonyl compound.

This secondary battery operates as described below.

During the battery charge, lithium ions are extracted from the positive electrode 21, and the extracted lithium ions are then inserted into the negative electrode 22 through the electrolytic solution. During the battery discharge, lithium ions are extracted from the negative electrode 22, and the extracted lithium ions are then inserted into the positive electrode 21 through the electrolytic solution.

This secondary battery is produced according to the following procedure.

The production of the positive electrode 21 starts with mixing, if necessary, a positive electrode active material with such a material(s) as a positive electrode binder and/or a positive electrode conductive material to prepare a positive electrode mixture. Then, the positive electrode mixture is dispersed in an organic solvent to form the positive electrode mixture into a pasty slurry. The prepared slurry is applied to both surfaces of the positive electrode current collector 21A and then dried to form the positive electrode active material layers 21B. Then, the positive electrode active material layers 21B are compressed, under heat if necessary, into a form by a roll pressing machine. The production may perform the compression more than once.

To produce the negative electrode 22, the negative electrode active material layer 22B is formed on both surfaces of the negative electrode current collector 22A according to steps similar to the steps described in connection with the positive electrode 21. Specifically, the negative electrode active material is mixed with such a material(s) as a negative positive electrode binder and/or a negative electrode conductive agent to prepare a negative electrode mixture. Then, the negative electrode mixture is dispersed in an organic solvent to form the negative electrode mixture into a pasty slurry. The prepared slurry is applied to both surfaces of the negative electrode current collector 22A and then dried to form the negative electrode active material layers 22B. Lastly, the negative electrode active material layers 22B are compressed into a form by, for example, a roll pressing machine.

To assemble a secondary battery, the positive electrode lead 25 is attached by, for example, welding to the positive electrode current collector 21A, and the negative electrode lead 26 is attached by, for example, welding to the negative electrode current collector 22A. Then, the positive electrode 21 and the negative electrode 22 are stacked in layers with the separator 23 interposed therebetween, and the positive electrode 21, negative electrode 22, and separator 23 are all together wound in a roll to form the rolled electrode 20. Then, the center pin 24 is inserted through the rolled electrode 20 at its center.

The rolled electrode 20 held between the paired insulating plates 12 and 13 is housed in the battery can 11. Then, an edge of the positive electrode lead 25 is attached by, for example, welding to the safety valve mechanism 15, and an edge of the negative electrode lead 26 is attached by, for example, welding to the battery can 11. The electrolytic solution is injected into the battery can 11 to impregnate the rolled electrode 20 with the electrolytic solution. Lastly, the battery lid 14, safety valve mechanism 15, and thermally sensitive resistor 16 are fixed by crimping to the opening end of the battery can 11 with the sealing gasket 17 interposed therebetween. As a result, the production of a cylindrical secondary battery is completed.

In this cylindrical lithium ion secondary battery, the electrolytic solution used therein is similar in composition to the electrolytic solution according to the technology disclosed herein. This may substantially inhibit decomposition reactions of the electrolytic solution during use (charge and discharge) and storage of the secondary battery. Such a secondary battery may excel in properties. Any other actions and effects expected may be similar to those described in connection with the electrolytic solution according to the technology disclosed herein.

Figure 3:
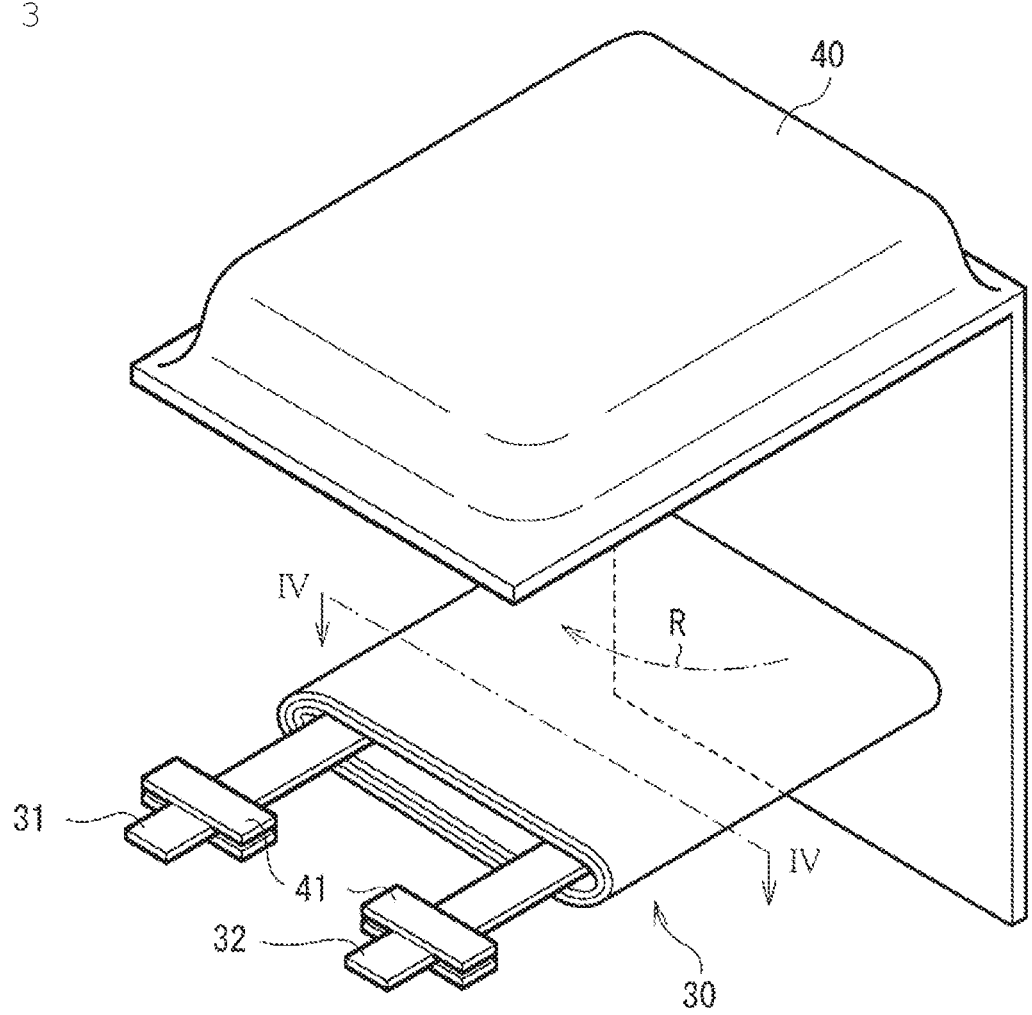
FIG. 3 is a perspective view of a secondary battery (battery in the form of a laminate film) according to an embodiment of the technology disclosed herein.
Figure 4:
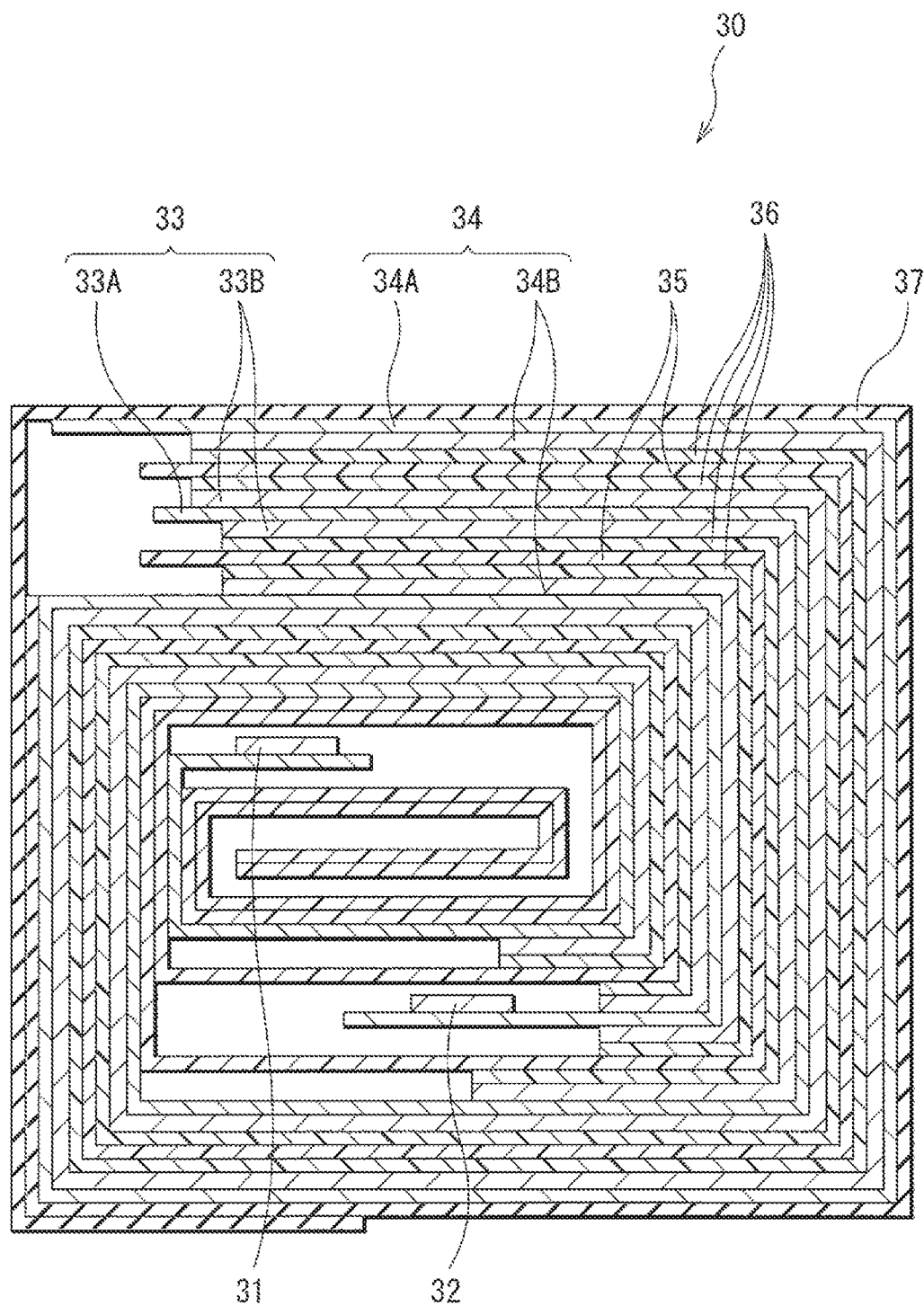
FIG. 4 is a cross-sectional view of a rolled electrode along IV-IV line illustrated in FIG. 3.

FIG. 3 is a cross-sectional view of another secondary battery. FIG. 4 is a cross-sectional view of a rolled electrode 30 along IV-IV line illustrated in FIG. 3. The rolled electrode 30 and a container member 40 are spaced part in the illustration of FIG. 3.

In the description of this secondary battery hereinafter given are used the structural elements of the cylindrical secondary battery.

This secondary battery is a lithium ion secondary battery in the form of a laminate film. In this battery, a rolled electrode 30 as cell element is housed in a container member 40 in a film-like shape, as illustrated in FIG. 3. The rolled electrode 30 is so structured that a positive electrode 33 and a negative electrode 34 are stacked in layers with a separator 35 and an electrolyte layer 36 interposed therebetween, and the positive electrode 33, negative electrode 34, and separator 35, and electrolyte layer 36 are all together wound in a roll. A positive electrode lead 31 is attached to the positive electrode 33, and a negative electrode lead 32 is attached to the negative electrode 34. The outermost peripheral part of the rolled electrode 30 is protected with a protective tape 37.

The positive electrode lead 31 and the negative electrode lead 32 are, for example, extended in the same direction from the inner side to the outer side of the container member 40. The positive electrode lead 31 may include one or two or more selected from conductive materials including aluminum (Al). The negative electrode lead 32 may include one or two or more selected from conductive materials including copper (Cu), nickel (Ni), and stainless steel. These conductive materials may be reticulate or have a thin-plate shape.

The container member 40 may be a film foldable in a direction indicated with arrow R in FIG. 3. The container member 40 may have, in its part, a dented part in which the rolled electrode 30 is containable. The container member 40 is a laminate film in which adhesive layers, a metal layer, and a surface protective layer are stacked on one another in the mentioned order. In the secondary battery production process, the container member 40 is folded so as to have the adhesive layers face each other across the rolled electrode 30, and outer peripheral edges of the adhesive layers are adhered to each other. The container member 40 may consist of two laminate films bonded to each other with, for example, an adhesive. The adhesive layers may be a film made of one or two or more selected from materials including polyethylene and polypropylene. The metal layer may be a foil made of one or two or more selected from metals including aluminum. The surface protective layer may be a film made of one or two or more selected from materials including nylon and polyethylene terephthalate.

A particularly preferable example of the container member 40 may be an aluminum laminate film in which a polyethylene film, an aluminum film, and a nylon film are stacked in layers in the mentioned order. The container member 40 may be any other multilayered laminate film, a polymer film made of polypropylene, or a metal film.

An adhesive film 41 is interposed between the container member 40 and the positive electrode lead 31 so as to block outside air. The adhesive film 41 is also interposed between the container member 40 and the negative electrode lead 32. The adhesive film 41 includes a material adherable to both of the positive electrode lead 31 and the negative electrode lead 32. Such a material adherable to these electrode leads may be a polyolefin resin. Specific examples of the material may be one or two or more selected from polyethylene, polypropylene, modified polyethylene, and modified polypropylene.

The positive electrode 33 may include a positive electrode current collector 33A and a positive electrode active material layer 33B. The negative electrode 34 may include a negative electrode current collector 34A and a negative electrode active material layer 34B. The positive electrode current collector 33A, positive electrode active material layer 33B, negative electrode current collector 34A, and negative electrode active material layer 34B may be configured similarly to the positive electrode current collector 21A, positive electrode active material layer 21B, negative electrode current collector 22A, and negative electrode active material layer 22B. The separator 35 may be configured similarly to the separator 23.

The electrolyte layer 36 includes an electrolytic solution and a high molecular compound. This electrolytic solution is similar in composition to the electrolytic solution according to the technology disclosed herein. As such, the electrolytic solution includes a sulfonyl compound. The electrolyte layer 36 described herein is a gelatinous electrolyte in which the electrolytic solution is retained by the high molecular compound. A high ion conductivity (for example, 1 mS/cm or more at room temperature) may be accordingly achievable, and leakage of such an electrolytic solution may be unlikely to occur. The electrolyte layer 36 may include one or two or more additional materials, for example, an additive(s).

The high molecular compound may include one or two or more selected from polyacrylonitrile, polyvinylidene fluoride, polytetrafluoroethylene, polyhexafluoropropylene, polyethylene oxides, polypropylene oxides, phosphazene, polysiloxane, polyvinyl fluoride, polyvinyl acetate, polyvinyl alcohol, methyl polymethacrylate, polyacrylate, polymethacrylate, styrene-butadiene rubbers, nitrile-butadiene rubbers, polystyrene, and polycarbonate. The high molecular compound may be a copolymer. The copolymer may be a vinylidene fluoride-hexafluoropyrene copolymer. A preferable monopolymer may be polyvinylidene fluoride, while a preferable copolymer may be a vinylidene fluoride-hexafluoropyrene copolymer. These materials may ensure electrochemical stability.

In the electrolyte layer 36 which is an gelatinous electrolyte, a solvent included in the electrolytic solution represents a broad concept encompassing different types of materials including liquid materials and materials having ion conductivity so as to detach electrolytic salt. When a high molecular compound having ion conductivity is used, the high molecular compound is also included in a non-aqueous solvent.

The electrolytic solution may be directly used instead of the electrolyte layer 36. In this instance, the rolled electrode 30 is impregnated with the electrolytic solution.

This secondary battery operates as described below.

During the battery charge, lithium ions are extracted from the positive electrode 33, and the extracted lithium ions are then inserted into the negative electrode 34 through the electrolyte layer 36. During the battery discharge, lithium ions are extracted from the negative electrode 34, and the extracted lithium ions are then inserted into the positive electrode 33 through the electrolyte layer 36.

A secondary battery including the gelatinous electrolyte layer 36 may be produced according to three different procedures.

In a first procedure, the positive electrode 33 and the negative electrode 34 are produced in a manner similar to the positive electrode 21 and the negative electrode 22. To produce the positive electrode 33, the positive electrode active material layer 33B is formed on both surfaces of the positive electrode current collector 33A. To produce the negative electrode 34, the negative electrode active material layer 34B is formed on both surfaces of the negative electrode current collector 34A. Next, the electrolytic solution, high molecular compound, and organic solvent are mixed to prepare a precursory solution. The prepared precursory solution is applied to the positive electrode 33 and then dried to form the gelatinous electrolyte layer 36. The prepared precursory solution is applied to the negative electrode 34 and then dried to form the gelatinous electrolyte layer 36. Then, the positive electrode lead 31 is attached by, for example, welding to the positive electrode current collector 33A, and the negative electrode lead 32 is attached by, for example, welding to the negative electrode current collector 34A. The positive electrode 33 and the negative electrode 34 are then stacked in layers with the separator 35 interposed therebetween, and the positive electrode 33, negative electrode 34, and separator 35 are all together wound in a roll to form the rolled electrode 30. The protective tape 37 is bonded to the outermost peripheral part of the rolled electrode 30. The container member 40 is folded with the rolled electrode 30 held therebetween, and outer peripheral edges of the container member 40 are adhered to each other by heat seal to enclose the rolled electrode 30 in the container member 40. In this procedure, the adhesive film 41 is inserted between the positive electrode lead 31 and the container member 40, and the adhesive film 41 is inserted between the negative electrode lead 32 and the container member 40.

In a second procedure, the positive electrode lead 31 is attached to the positive electrode 33, and the negative electrode lead 32 is attached to the negative electrode 34. The positive electrode 33 and the negative electrode 34 are stacked in layers with the separator 35 interposed therebetween to obtain a precursory rolled body that will constitute the rolled electrode 30. Then, the protective tape 37 is bonded to the outermost peripheral part of the rolled body. The container member 40 is folded with the rolled electrode 30 held therebetween, and outer peripheral edges, except an edge on one side, of the container member 40 are thermally adhered to each other to locate the rolled body in the bag-like container member 40. The electrolytic solution is mixed with other materials including a monomer, raw material of the high molecular compound, a polymerization initiator, and, if necessary, a polymerization inhibitor to prepare an electrolyte composition. After the electrolyte composition is injected into the bag-like container member 40, the container member 40 is tightly closed by heat seal. Then, the monomer is thermally polymerized to form the high molecular compound. Thus, the electrolytic solution is retained by the high molecular compound, and the gelatinous electrolyte layer 36 is formed.

In a third procedure, a rolled body is produced and located in the bag-like container member 40 similarly to the second procedure, except that a separator 35 is used that includes high molecular compound layers formed thereon. After the electrolytic solution is prepared and injected into the bag-like container member 40, the opening of the container member 40 is tightly closed by heat seal. The container member 40 is then heated with a weight imposed thereon to force the separator 35 into close contact with the positive electrode 33 across the high molecular compound layer and also to force the separator 35 into close contact with the negative electrode 34 across the high molecular compound layer. Thus, the high molecular compound layers are impregnated with the electrolytic solution and thereby gelatinized. As a result, the electrolyte layer 36 is formed.

The third procedure may suppress possible swelling of the secondary battery, as compared with the first procedure. As compared with the second procedure, the third procedure barely leaves the monomer and non-aqueous solvent (raw material of the high molecular compound) in the electrolyte layer 36, allowing well-controlled production of the high molecular compound. This may allow the electrolyte layer 36 to very closely contact the positive electrode 33, negative electrode 34, and separator 35.

In the lithium ion secondary battery formed like a laminate film, the electrolyte layer 36 includes the electrolytic solution which is similar in composition to the electrolytic solution according to the technology disclosed herein. This secondary battery, therefore, may excel in properties for the same reasons as described in connection with the cylindrical lithium ion secondary battery. Any other actions and effects expected may be similar to those described in connection with the cylindrical lithium ion secondary battery.

The secondary battery hereinafter described is a cylindrical lithium metal secondary battery in which the capacity of the negative electrode 22 is obtainable through deposition and dissolution of lithium metal. This secondary battery is configured similarly to the cylindrical lithium ion secondary battery described earlier and is produced according to a similar procedure. This secondary battery, however, differs from the earlier secondary battery in that lithium metal is used to form the negative electrode active material layer 22B.

This secondary battery using lithium metal as the negative electrode active material may obtain higher energy density. The negative electrode active material layer 22B may be formed in advance before the assembling starts, or may be formed later after the assembling starts using lithium metal deposited during the battery charge. The negative electrode active material layer 22B may be used as current collector, in which case the negative electrode current collector 22A may be unnecessary.

This secondary battery operates as described below. During the battery charge, lithium ions are extracted from the positive electrode 21, and the extracted lithium ions are then deposited as lithium metal on the surface of the negative electrode current collector 22A through the electrolytic solution. During the battery discharge, lithium metal deposited on the negative electrode active material layer 22B elutes off, as lithium ions, into the electrolytic solution and then inserted into the positive electrode 21 through the electrolytic solution.

In this cylindrical lithium metal secondary battery, the electrolytic solution is similar in composition to the electrolytic solution according to the technology disclosed herein. This secondary battery, therefore, may excel in properties for the same reasons as described in connection with the lithium ion secondary battery described earlier. Any other actions and effects expected may be similar to those described earlier in connection with the lithium ion secondary battery.

The configuration of this lithium metal secondary battery may be applied to the laminate film-type secondary battery instead of the cylindrical secondary battery. In this instance, a similar effect may be obtained Next, applications of the secondary battery are hereinafter described.

The secondary battery may be unlimitedly applicable to any objects including machines, devices, tools, apparatuses, and systems (where plural devices and/or apparatuses are combined) in which the secondary battery is usable as power source to drive such objects or as power storage for such objects. The secondary battery serving as power source may be either a main power source or an auxiliary power source. The main power source is given priority for use over any other power sources regardless of whether they are available. The auxiliary power source may be an alternative power source that can replace the main power source or may be a power source selected over the main power source whenever necessary. In case the secondary battery is used as the auxiliary power source, the main power source is not limited to the secondary battery.

Exemplified applications of the secondary battery may be the following electronic devices (including mobile electronic devices); video cameras, digital still cameras, mobile telephones, laptop computers, cordless telephones, headset stereo devices, mobile radios, mobile televisions, and personal digital assistants; and portable devices for daily use such as electric shavers. Other applications of the secondary battery may include the following: storages including backup power source and memory cards; electrically driven tools including electric drills and electric saws; battery packs mountable in, for example, laptop personal computers as removable power source; medical electronic devices including pacemakers and hearing aids; electrically driven vehicles including electric automobiles (including hybrid cars); and power storage systems, like home battery systems, used as power storage in case of emergency. It should be understood that possible applications of the secondary battery may include other fields of use.

Among the examples, the secondary battery may be particularly useful when applied to battery packs, electrically driven vehicles, power storage systems, electrically driven tools, and electronic devices. When the secondary battery according to the technology disclosed herein is used in such applications that demand excellent battery properties, significant improvement in performance may be expected. The battery pack is a power source using the secondary battery. As described later, either a unit cell or a battery module may be used in the battery pack. The electrically driven vehicle is a vehicle that uses the secondary battery as power source to operate (run), which may be, as described earlier, an automobile equipped with a driving source in combination with the secondary battery (hybrid automobile). The power storage system is a system using the secondary battery to store power. In a home power storage system, for example, electricity is stored in the secondary battery and then used to drive home electric appliances. The electrically driven tool uses the secondary battery as power source to drive its movable part (for example, drill). The electronic device uses the secondary battery as power source (power supply) to fulfill its functions.

Some of the applications of the secondary battery are hereinafter described in detail. The applications hereinafter described are only given by way of example, specifics of which may be optionally modified.

Figure 5:
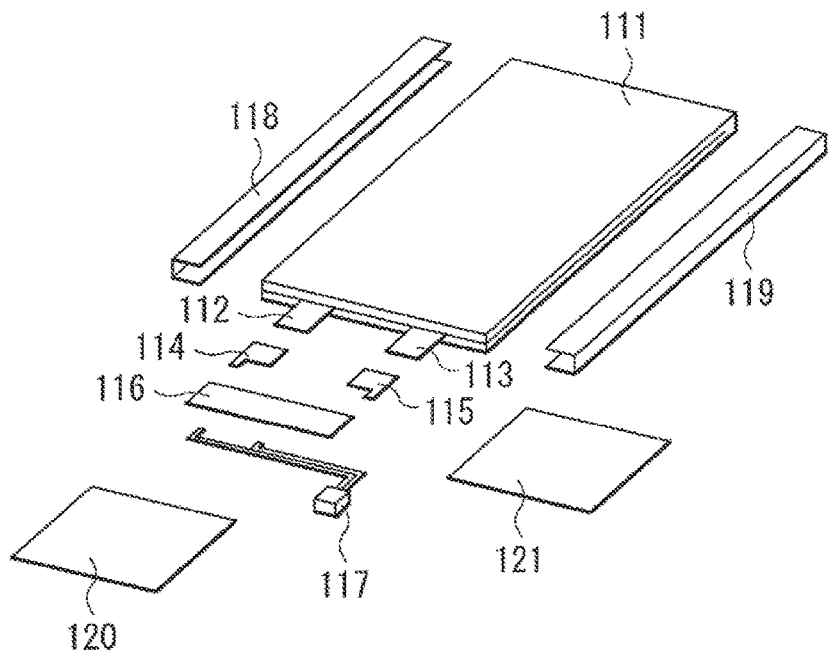
FIG. 5 is a perspective view illustrating an exemplified application of the secondary battery (battery pack: unit cell) according to an embodiment of the present technology.
Figure 6:
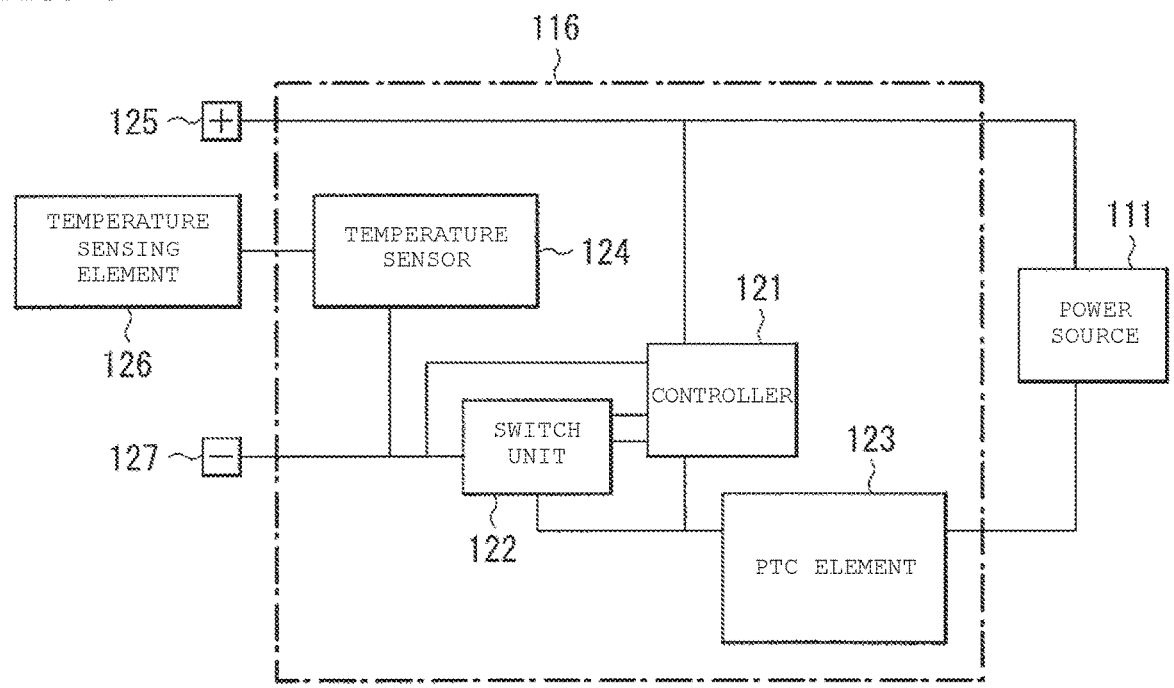
FIG. 6 is a block diagram of the battery pack illustrated in FIG. 5.

FIG. 5 is a perspective view of a battery pack using a unit cell. FIG. 6 is a block diagram of the battery pack illustrated in FIG. 5. FIG. 5 shows the battery pack in an exploded view.

The battery pack hereinafter described is a simple battery pack using one secondary battery according to the technology disclosed herein (generally called soft pack battery), which is generally used in electronic devices, typically, in smart phones. As illustrated in FIG. 5, this battery pack includes a power source 111, laminate film-type secondary battery, and a circuit board 116 coupled to the power source 111. A positive electrode lead 112 and a negative electrode lead 113 are attached to the power source 111.

A pair of sticky tapes 118 and 119 are bonded to both side surfaces of the power source 111. The circuit board 116 includes a protective circuit (PCM: Protection Circuit Module). The circuit board 116 is coupled to the positive electrode 112 through a tab 114 and is coupled to the negative electrode lead 113 through a tab 115. The circuit board 116 is further coupled to a lead wire 117 with a connector for external connection. The circuit board 116 being coupled to the power source 111 is protected with a label 120 and an insulating sheet 121. The label 120 being attached allows the circuit board 116 and the insulating sheet 121 to be immovably positioned.

As illustrated in FIG. 6, the battery pack includes, for example, the power source 111 and the circuit board 116. The circuit board 116 may include a controller 121, a switch unit 122, a PTC element 123, and a temperature sensor 124. The power source 111 is connectable to external equipment through a positive electrode terminal 125 and a negative electrode terminal 127 and is accordingly chargeable and dischargeable through the positive electrode terminal 125 and the negative electrode terminal 127. The temperature sensor 124 performs temperature detection using a temperature sensing terminal (generally called T terminal) 126.

The controller 121 controls the operation of the whole battery pack (including a current state of use of the power source 111). The controller 121 may include a central processing unit (CPU) and a memory.

When the battery voltage reaches a voltage value indicative of overcharge detection, the controller 121 may interrupt the switch unit 122 to prevent charging current from flowing into the current path of the power source 111. In case a large current flows during the battery charge, the controller 121 may interrupt the switch unit 122 to block the flow of charging current.

When the battery voltage reaches a voltage value indicative of overdischarge detection, the controller 121 may interrupt the switch unit 122 to prevent discharging current from flowing into the current path of the power source 111. In case a large current flows during the battery discharge, the controller 121 may interrupt the switch unit 122 to block the flow of discharging current.

The overcharge detection voltage may be 4.2 V±0.05 V, and the overdischarge detection voltage may be 2.4 V±0.1 V.

As prompted by the controller 121, the switch unit 122 changes the state of use of the power source 111, i.e., connects or disconnects the power source 111 to and from external equipment. The switch unit 122 may include a charging control switch and a discharging control switch. The charging control switch and the discharging control switch may be semiconductor switches, for example, field effect transistors (MOSFET) using a metal oxide semiconductor. The charging and discharging currents may be detected based on the ON-resistance of the switch unit 122.

The temperature sensor 124 measures the temperature of the power source 111 and outputs the measured temperature to the controller 121. The temperature sensor 124 may include a temperature sensing element such as thermistor. The temperature measured by the temperature sensor 124 may be used at the time of charging/discharging control by the controller 121 for overheat detection, and at the time of any necessary correction by the controller 121 of a calculated remaining battery level.

The circuit board 116 may be unequipped with the PTC element 123. In this instance, a PTC element may be separately attached to the circuit board 116.

Figure 7:
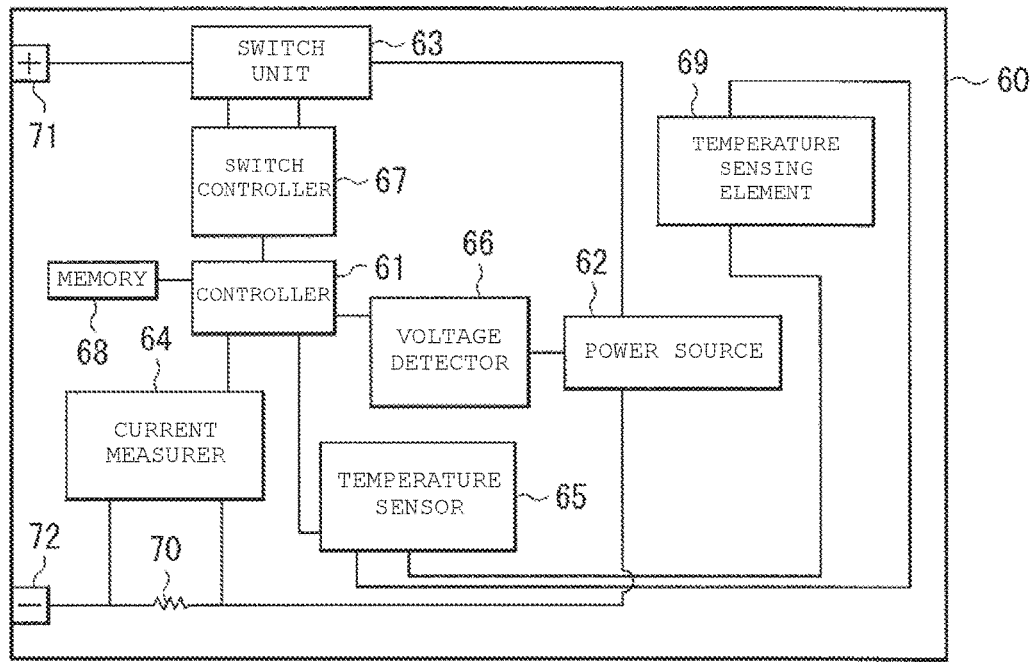
FIG. 7 is a block diagram illustrating an exemplified application of the secondary battery (battery pack: battery module) according to an embodiment of the present technology.

FIG. 7 is a block diagram of a battery pack using a battery module.

This battery pack may include, in a cabinet 60, a controller 61, a power source 62, a switch unit 63, a current measurer 64, a temperature sensor 65, a voltage detector 66, a switch controller 67, a memory 68, a temperature sensing element 69, a current detecting resistance 70, a positive electrode terminal 71, and a negative electrode terminal 72. The cabinet 60 may include a plastic material.

The controller 61 controls the operation of the whole battery pack (including a current state of use of the power source 62). The controller 61 may include CPU. The power source 62 is a battery module including two or more different types of secondary batteries according to the technology disclosed herein. The two or more different types of secondary batteries may be interconnected in series or in parallel or in series-parallel combined arrangement. For example, the power source 62 includes six secondary batteries that are interconnected in 2-parallel and 3-series arrangement.

As prompted by the controller 61, the switch unit 63 changes the state of use of the power source 62, i.e., connects or disconnects the power source 62 to and from external equipment. The switch unit 63 may include a charging control switch, a discharging control switch, a charging diode, and a discharging diode. The charging control switch and the discharging control switch may be semiconductor switches, for example, field effect transistors (MOSFET) using a metal oxide semiconductor.

The current measurer 64 measures electric current using the current detecting resistance 70 and outputs the measured current to the controller 61. The temperature sensor 65 measures the temperature using the temperature sensing element 69 and outputs the measured temperature to the controller 61. The measured temperature thus obtained may be used at the time of charging/discharging control by the controller 61 for overheat detection, and at the time of any necessary correction by the controller 61 of a calculated remaining battery level. The voltage detector 66 measures the voltage of the secondary battery in the power source 62 and feeds the controller 61 with the measured voltage that has been subjected to analog-digital conversion.

The switch controller 67 controls the operation of the switch unit 63 in response to input signals received from the current measurer 64 and the voltage detector 66.

When the battery voltage reaches a voltage value indicative of overcharge detection, the switch controller 67 may interrupt the switch unit 63 (charging control switch) to prevent charging current from flowing into the current path of the power source 62. Then, discharging through the discharging diode alone may be allowed for the power source 62. In case a large current flows during the battery charge, the switch controller 67 may block the flow of charging current.

When the battery voltage reaches a voltage value indicative of overdischarge detection, the switch controller 67 may interrupt the switch unit 63 (discharging control switch) to prevent discharging current from flowing into the current path of the power source 62. Then, charging through the charging diode alone may be allowed for the power source 62. In case a large current flows during the battery discharge, the switch controller 67 may block the flow of discharging current.

The overcharge detection voltage may be 4.2 V±0.05 V, and the overdischarge detection voltage may be 2.4 V±0.1 V.

The memory 68 may include EEPROM which is a nonvolatile memory. In the memory 68 are prestored, for example, values calculated by the controller 61 and information of the secondary battery measured during the production process (for example, initial internal resistance). When the full-charge capacity of the secondary battery is stored in the memory 68, the controller 61 is allowed to determine information including a current remaining battery level.

The temperature sensing element 69 measures the temperature of the power source 62 and outputs the measured temperature to the controller 61. The temperature sensing element 69 may include a thermistor.

The positive electrode terminal 71 and the negative electrode terminal 72 are each a terminal coupled to external equipment operated with the battery pack (for example, laptop personal computer) or external equipment used to charge the battery pack (for example, charger). The power source 62 is charged and discharged through the positive electrode terminal 71 and the negative electrode terminal 72.

Figure 8:
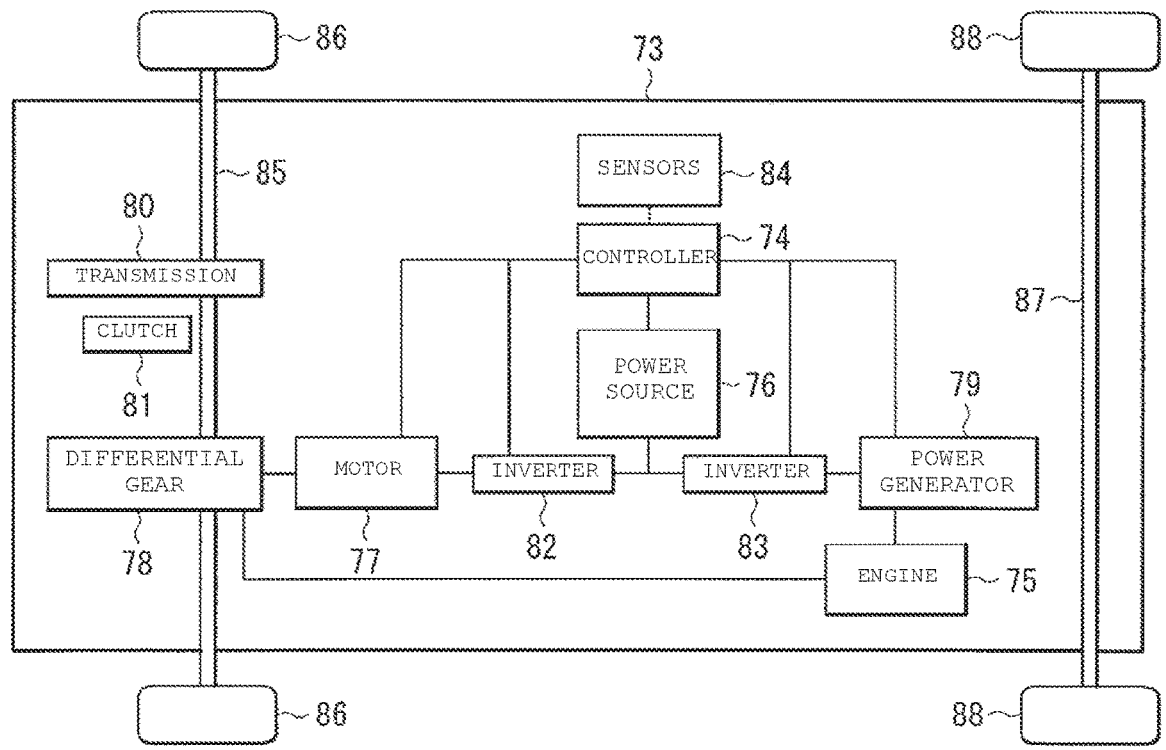
FIG. 8 is a block diagram illustrating an exemplified application of the secondary battery (electrically driven vehicle) according to an embodiment of the present technology.

FIG. 8 is a block diagram of a hybrid automobile which is an example of the electrically driven vehicle.

This electrically driven vehicle may include, in a metallic cabinet 73, a controller 74, an engine 75, a power source 76, a motor 77 that drives the vehicle, a differential gear 78, a power generator 79, a transmission 80, a clutch 81, inverters 82 and 83, and different types of sensors 84. The electrically driven vehicle may further include a front wheel driving shaft 85, a front wheel 86, a rear wheel driving shaft 87, and a rear wheel 88 that are coupled to the differential gear 78 and the transmission 80.

This electrically driven vehicle may be driven to run by one of the engine 75 and the motor 77 used as driving source. The engine 75 is the main source of motive power, an example of which may be a gasoline engine. When the motive power source is the engine 75, the driving force of the engine 75 (rotary force) may be transmitted to the front wheel 86 and the rear wheel 88 through the driving components, differential gear 78, transmission 80, and clutch 81. The rotary force of the engine 75 is transmitted to the power generator 79 and is used by the power generator 79 to generate alternating current power. The alternating current power is then converted through the inverter 83 into direct current power. Then, the direct current power is stored in the power source 76. When the motor 77, which is a converter component, is the motive power source, power supplied from the power source 76 (direct current power) is converted through the inverter 82 into alternating current power. Then, the alternating current power is used to drive the motor 77. The driving force (rotary force) obtained by conversion of power by the motor 77 may be transmitted to the front wheel 86 and the rear wheel 88 through the driving components, differential gear 78, transmission 80, and clutch 81.

When the electrically driven vehicle is decelerated by a braking mechanism, a resistance force during the deceleration is transmitted as rotary force to the motor 77. The rotary force may be used by the motor 77 to generate alternating current power. The alternating current power is converted into direct current power through the inverter 82. Regenerated energy of the direct current power may preferably be stored in the power source 76.

The controller 74 controls the operation of the whole electrically driven vehicle. The controller 74 may include CPU. The power source 76 includes one or two or more different types of secondary batteries according to the technology disclosed herein. The power source 76 may be coupled to an external power source so as to receive electric power supplied from the external power source and store the received electric power. The sensors 84 may be used to control the engine speed of the engine 75 and to control the opening degree of a throttle valve (throttle opening degree). The sensors 84 may include one or two or more of a speed sensor, an acceleration sensor, and an engine speed sensor.

In the description above, the electrically driven vehicle is a hybrid automobile. The electrically driven vehicle may be a vehicle operated by the use of the power source 76 and the motor 77 alone without the engine 75 (electric automobile).

Figure 9:
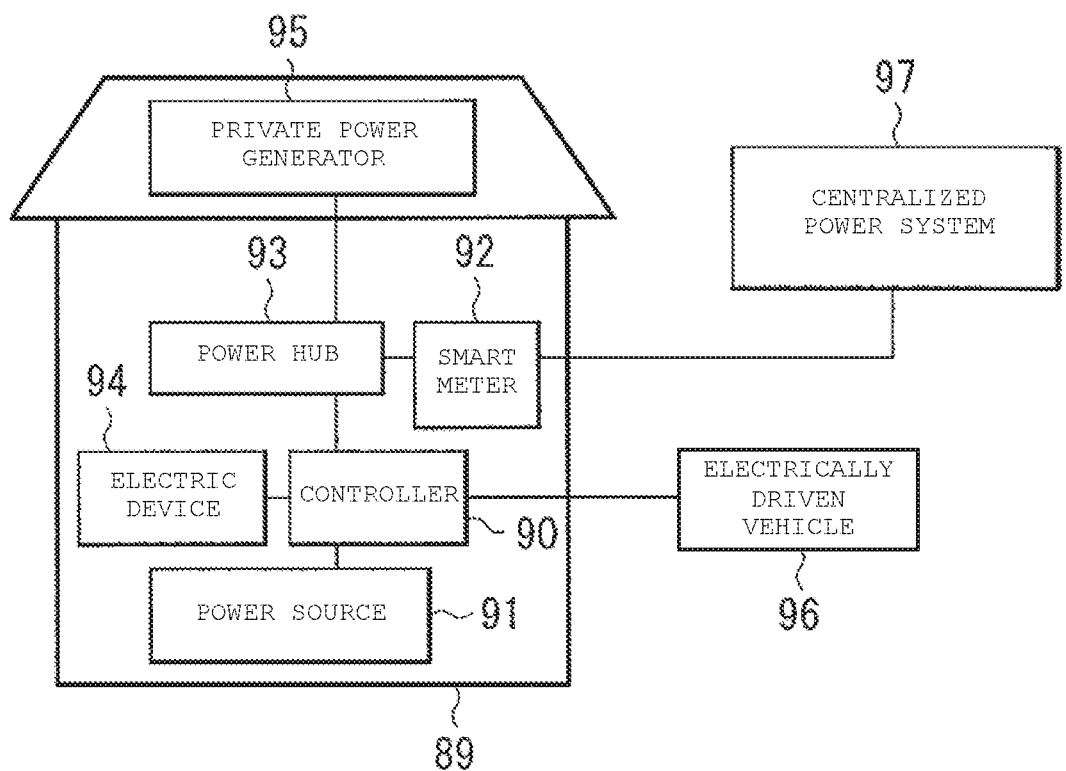
FIG. 9 is a block diagram illustrating an exemplified application of the secondary battery (power storage system) according to an embodiment of the present technology.

FIG. 9 is a block diagram of a power storage system.

This power storage system may be for use in a building 89, for example, a residence or commercial premises, and includes a controller 90, a power source 91, a smart meter 92, and a power hub 93.

The power source 91 may be connected to an electric device 94 installed in the building 89 and may also be connected to an electrically driven vehicle 96 parked outside the building 89. The power source 91 may be coupled to a private power generator 95 installed in the building 89 through the power hub 93 and may also be connected to an external centralized power system 97 through the smart meter 92 and the power hub 93.

The electric device 94 may include one or two or more home electric appliances, for example, refrigerator, air conditioner, television, and water heater. The private power generator 95 may include one or two or more power generators, for example, solar power generator and wind power generator. The electrically driven vehicle 96 may include one or two or more vehicles, for example, electric automobile, electric motorcycle, and hybrid automobile. The centralized power system 97 may include one or two or more power plants, for example, thermal power plant, atomic power plant, hydraulic power plant, and wind power plant.

The controller 90 controls the operation of the whole power storage system (including a current state of use of the power source 91). The controller 90 may include CPU. The power source 91 includes one or two or more different types of secondary batteries according to the technology disclosed herein. The smart meter 92 may be a network-accessible wattmeter installed in the building 89 that is a power demand side and allowed to communicate with a power supply side. The smart meter 92 thus configured may enable highly-efficient and stable energy supply by controlling a balance between supply and demand in the building 89 through communication with outside.

In the power storage system, electric power supplied from the centralized power system 97; external power source, is stored in the power source 91 through the smart meter 92 and the power hub 93, and electric power generated by the private power generator 95; independent power source, is stored in the power source 91 through the power hub 93. As prompted by the controller 90, the power stored in the power source 91 is supplied to the electric device 94 and the electrically driven vehicle 96 to allow the electric device 94 to operate and also allow the electrically driven vehicle 96 to be charged. Thus, the power storage system may allow electric power to be stored in and supplied to the building 89 using the power source 91.

The power stored in the power source 91 may be used in response to the needs. For example, electric power supplied from the centralized power system 97 may be stored in the power source 91 during nighttime when electricity rate is cheaper, and the electric power stored in the power source 91 may be used during daytime slots when the electricity rate is higher.

The power storage system described above may be installed for each individual housing (one household) or may be installed for a plurality of individual housings (multiple households).

Figure 10:
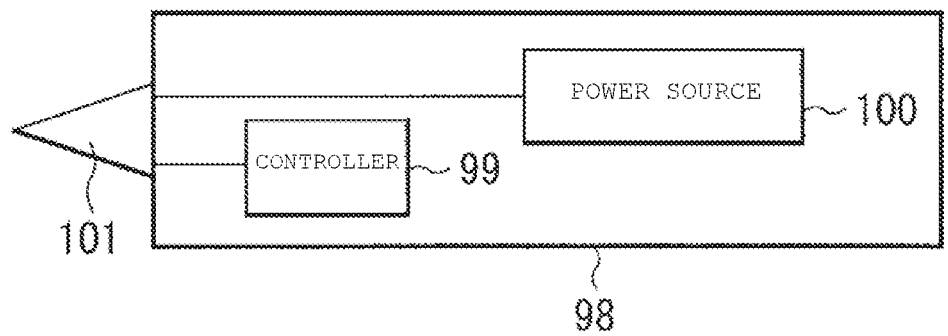
FIG. 10 is a block diagram illustrating an exemplified application of the secondary battery (electrically driven tool) according to an embodiment of the present technology.

FIG. 10 is a block diagram of an electrically driven tool.

The electrically driven tool described herein may be an electric drill. This electrically driven tool may include, in its body 98, a controller 99 and a power source 100. A movable drill unit 101 is operably (rotatably) attached to the body 98.

The body 98 may include a plastic material. The controller 99 controls the operation of the whole electrically driven tool (including a current state of use of the power source 100). The controller 99 may include CPU. The power source 100 includes one or two or more different types of secondary batteries according to the technology disclosed herein. The controller 99 supplies the drill unit 101 with electric power from the power source 100 in response to an operation switch being manipulated.

Working examples of the technology disclosed herein are hereinafter described.

Experimental Examples 1-33

Lithium ion secondary batteries in the form of a laminate film illustrated in FIGS. 3 and 4 were produced according to the steps described below.

The production of the positive electrode 33 started with mixing lithium carbonate ($Li_2CO_3$) and cobalt carbonate ($CoCO_3$) with each other. Then, the obtained mixture was fired (firing temperature: 900° C., firing time: 5 hours) to obtain a lithium-containing compound; lithium cobalt oxide ($LiCoO_2$). The mixing ratio of lithium carbonate and cobalt carbonate then (molar ratio) was lithium carbonate:cobalt carbonate=0.5:1.

Next, the following materials were mixed to prepare a positive electrode mixture; 91 parts by mass of the positive electrode active material (lithium cobalt oxide), 3 parts by mass of a positive electrode binder (polyvinylidene fluoride), and 6 parts by mass of a positive electrode conductive material (graphite). Then, the positive electrode mixture was added to an organic solvent (N-methyl-2-pyrrolidone), and the resulting organic solvent was stirred to form the positive electrode mixture into a pasty slurry. The prepared slurry was applied to both surfaces of the positive electrode current collector 33A (aluminum foil of 12 μm in thickness) by a coating device and then dried to form the positive electrode active material layer 33B. Lastly, the positive electrode active material layer 33B was compressed into a form by a roll pressing machine.

The production of the negative electrode 34 started with mixing the following materials to prepare a negative electrode mixture; 96 parts by mass of a negative electrode active material (graphite, median diameter: 15 μm), 1.5 parts by mass of a negative electrode binder (acrylic modified styrene-butadiene rubber copolymer), and 1.5 parts by mass of a thickener (carboxymethyl cellulose). This negative electrode mixture was added to pure water, and the resulting pure water was stirred to form the negative electrode mixture into a pasty slurry. The prepared slurry was applied to both surfaces of the negative electrode current collector 34A (band-shaped copper foil of 15 μm in thickness) by a coating device and then dried to form the negative electrode active material layer 34B. Lastly, the negative electrode active material layer 34B was compressed into a form by a roll pressing machine.

Electrolytic solutions were prepared as described below. An electrolytic salt ($LiPF_6$) was added to a solvent (ethylene carbonate and propylene carbonate), and the resulting solvent was stirred. Then, a sulfonyl compound (first sulfonyl compound, second sulfonyl compound) was further added to this solvent, and the resulting solvent was stirred again. The mixing ratio (mass ratio) of ethylene carbonate and propylene carbonate then was ethylene carbonate:propylene carbonate=50:50. The content of the electrolytic salt in the solvent was 1.2 mol/kg. Table 1 shows types of the sulfonyl compounds used and contents of the sulfonyl compounds in the electrolytic solutions (wt. %).

Electrolytic solutions for comparison were prepared according to similar steps, except that the sulfonyl compound was not used. Further, electrolytic solutions for comparison were prepared according to similar steps, except that other compounds were used instead of the sulfonyl compounds. Table 2 shows types of the other compounds used and contents of the other compounds in the electrolytic solutions (wt. %).

As a first step of assembling a secondary battery, the aluminum-made positive electrode lead 31 was welded to the positive electrode current collector 33A, and the copper-made negative electrode lead 32 was welded to the negative electrode current collector 34A. Next, the positive electrode 33 and the negative electrode 34 were stacked in layers with the separator 35 (microporous polyethylene film of 12 μm in thickness) interposed between these electrodes to obtain a laminate. Then, the laminate was rolled in its longitudinal direction, and the protective tape 37 was bonded to outermost peripheral parts of the laminate to obtain the rolled electrode 30. Lastly, the container member 40 was folded with the rolled electrode 30 held therebetween, and outer peripheral edges on three sides of the container member 40 were closed by heat seal. The container member 40 was an aluminum laminate film in which a 25 μm-thick nylon film, a 40 μm-thick aluminum foil, and a 30 μm-thick polypropylene film were stacked in layers in this order. The adhesive film 41 was inserted between the positive electrode lead 31 and the container member 40 and was also inserted between the negative electrode lead 32 and the container member 40. Lastly, the electrolytic solution was injected into the container member 40 and penetrated into the separator 35. Then, the unsealed outer peripheral edges on one side of the container member 40 were closed by heat seal under a reduced pressure. As a result, the rolled electrode 30 was sealed in the container member 40, and the production of a lithium ion secondary battery in the form of a laminate film was completed.

To evaluate the properties of the produced secondary batteries, their storage characteristics and swelling properties were examined. Tables 1 and 2 show the obtained results.

For storage characteristics, the secondary battery was first charged and discharged (two cycles) at normal temperature (=23° C.), and its discharge capacity at the second cycle (discharge capacity before storage) was measured. The secondary battery was charged again, and the charged secondary battery was stored at a high temperature (=60° C.) in a temperature-controlled bath (duration of storage=10 days). The secondary battery was then removed from the temperature-controlled bath and discharged at normal temperature (=23° C.), and its discharge capacity at the third cycle (discharge capacity after storage) was measured. The final step was to calculate values from the formula; high-temperature capacity maintenance factor (%)=((discharge capacity after storage)/(discharge capacity before storage))×100.

As for the battery charge, constant-current charge was performed until the voltage of 4.2 V was reached at the current of 0.2 C, followed by constant-voltage charge until the current of 0.05 C was reached at the voltage of 4.2 V. As for the battery discharge, constant-current discharge was performed until the voltage of 2.5 V was reached at the current of 0.2 C. The "0.2 C", represents a current value at which the battery capacity (theoretical capacity) is fully discharged in five hours, and the "0.05 C" represents a current value at which the battery capacity is fully discharged in 20 hours.

To examine swelling properties, the secondary battery was charged and discharged (two cycles) at normal temperature (=23° C.). Then, the secondary battery was immersed in an ethanol bath, and the volume of the secondary battery (volume ($cm^3$) before storage) was measured. The secondary battery was removed from the ethanol bath and then adequately dried. The secondary battery was charged again, and the charged secondary battery was stored at a high temperature (=60° C.) in a temperature-controlled bath (duration of storage=10 days). The secondary battery was removed from temperature-controlled bath and immersed in an ethanol solution again. Then, the volume of the secondary battery (volume after storage) was measured. The final step was to calculate values from the formula; high-temperature volume change factor (%)=((volume after storage)/(volume before storage))×100. This high-temperature volume change factor represents a generally called coefficient of expansion of the secondary battery.

Charging and discharging conditions similar to those employed for the storage characteristics were used to examine the swelling properties.

Criteria for comparison used in the description below were the high-temperature capacity maintenance factor and the high-temperature volume change factor obtained in the example in which neither of the sulfonyl compound nor any other compound was used (Experimental Example 22).

The examples in which the other compounds were used (Experimental Examples 23 to 33) showed decreases in the high-temperature capacity maintenance factor. On the other hand, the high-temperature volume change factor decreased with some of the other compounds, however, to a small

TABLE 1

| Experimental Examples | First sulfonyl compound Type | Content (wt. %) | Second sulfonyl compound Type | Content (wt. %) | Other compounds Type | Content (wt. %) | High-temperature capacity maintenance factor (%) | High-temperature volume change factor (%) |
|---|---|---|---|---|---|---|---|---|
| 1 | Formula (2-1) | 0.1 | — | — | — | — | 75 | 135 |
| 2 |  | 0.5 | — | — | — | — | 75 | 109 |
| 3 |  | 1 | — | — | — | — | 80 | 110 |
| 4 |  | 3 | — | — | — | — | 75 | 115 |
| 5 |  | 5 | — | — | — | — | 75 | 120 |
| 6 | Formula (2-2) | 1 | — | — | — | — | 77 | 111 |
| 7 | Formula (2-3) | 1 | — | — | — | — | 76 | 115 |
| 8 | Formula (2-4) | 1 | — | — | — | — | 76 | 120 |
| 9 | Formula (2-5) | 1 | — | — | — | — | 75 | 121 |
| 10 | Formula (2-6) | 1 | — | — | — | — | 75 | 118 |
| 11 | Formula (2-11) | 1 | — | — | — | — | 75 | 112 |
| 12 | Formula (2-12) | 1 | — | — | — | — | 79 | 111 |
| 13 | Formula (2-14) | 1 | — | — | — | — | 79 | 113 |
| 14 | Formula (2-19) | 1 | — | — | — | — | 79 | 110 |
| 15 | — | — | Formula (3-1) | 1 | — | — | 76 | 115 |
| 16 | — | — | Formula (3-2) | 1 | — | — | 75 | 113 |
| 17 | — | — | Formula (3-3) | 1 | — | — | 75 | 125 |
| 18 | — | — | Formula (3-4) | 1 | — | — | 76 | 114 |
| 19 | — | — | Formula (3-5) | 1 | — | — | 76 | 119 |
| 20 | — | — | Formula (3-6) | 1 | — | — | 78 | 115 |
| 21 | — | — | Formula (3-7) | 1 | — | — | 79 | 110 |

TABLE 2

| Experimental Examples | First sulfonyl compound Type | Content (wt. %) | Second sulfonyl compound Type | Content (wt. %) | Other compounds Type | Content (wt. %) | High-temperature capacity maintenance factor (%) | High-temperature volume change factor (%) |
|---|---|---|---|---|---|---|---|---|
| 22 | — | — | — | — | — | — | 74 | 151 |
| 23 | — | — | — | — | Formula (16-1) | 1 | 70 | 170 |
| 24 | — | — | — | — | Formula (16-2) | 1 | 68 | 160 |
| 25 | — | — | — | — | Formula (16-3) | 1 | 69 | 164 |
| 26 | — | — | — | — | Formula (16-4) | 1 | 71 | 160 |
| 27 | — | — | — | — | Formula (16-5) | 1 | 73 | 152 |
| 28 | — | — | — | — | Formula (16-6) | 1 | 66 | 170 |
| 29 | — | — | — | — | Formula (16-7) | 1 | 67 | 162 |
| 30 | — | — | — | — | Formula (16-8) | 1 | 68 | 160 |
| 31 | — | — | — | — | Formula (16-9) | 1 | 70 | 170 |
| 32 | — | — | — | — | Formula (16-10) | 1 | 69 | 160 |
| 33 | — | — | — | — | Formula (16-11) | 1 | 69 | 163 |

In the examples in which the sulfonyl compound was used (Experimental Examples 1 to 21), the high-temperature capacity maintenance factor and the high-temperature volume change factor were both improved, as compared with the examples in which the sulfonyl compounds was not used (Experimental Examples 22 to 33).

In the examples in which neither of the sulfonyl compound nor any other compound was used (Experimental Example 22), the high-temperature capacity maintenance factor to a certain extent was achieved, while the high-temperature volume change factor excessively increased.

extent. In most of these examples, the high-temperature volume change factor significantly increased.

In the examples in which the sulfonyl compound was used (Experimental Examples 1 to 21), on the other hand, the high-temperature capacity maintenance factor increased, while the high-temperature volume change factor significantly decreased, irrespective of which sulfonyl compound was used (first sulfonyl compound, second sulfonyl compound). In some of these examples in which the content of the sulfonyl compound in the electrolytic solution was 0.1 wt % to 5 wt %, the high-temperature volume change factor substantially decreased, with increases in the high-temperature capacity maintenance factor.

The results shown in Tables 1 and 2 demonstrate that the sulfonyl compound-containing electrolytic solution improves the storage characteristics and swelling properties. As a result, secondary batteries that excel in properties were obtained.

While the technology disclosed herein was thus far described in connection with the embodiment and working examples, the technology is not necessarily limited to the aspects described in these embodiment and working examples. The scope of the technology disclosed herein may include many other modifications.

While the secondary batteries described herein have a cylindrical structure and a laminate film-like structure, the secondary battery according to the technology disclosed herein may be structured otherwise. Specific examples may include an angular structure and a coin-like structure.

While the battery elements are wound in a roll in this description, the battery elements of the secondary battery according to the technology disclosed herein may be formed otherwise. For example, the battery elements may be provided in a multilayered structure.

So far was described the secondary battery in which the capacity of the negative electrode is obtainable through insertion and extraction of lithium (lithium ion secondary battery) and the secondary battery in which the capacity of the negative electrode is obtainable through deposition and dissolution of lithium (lithium metal secondary battery). In the secondary battery according to the technology disclosed herein, the mechanism of obtaining the capacity of the negative electrode is not particularly limited. In a specific example of the secondary batteries configured otherwise, the capacity of the negative electrode material that can insert and extract lithium may be set to a smaller capacity than that of the positive electrode. Then, capacities obtainable through lithium insertion and extraction and obtainable through lithium deposition and dissolution may be summed to obtain the capacity of the negative electrode.

In the description given earlier, the electrode reaction material is lithium, however, is not necessarily limited thereto. Other example of the electrode reaction material may include the other Group 1 elements, such as sodium (Na) and potassium (K), in the long-form periodic table, and Group 2 elements, such as magnesium (Mg) and calcium (Ca), in the long-form periodic table, and light metals such as aluminum (Al). The electrode reaction material may be an alloy including one or two or more selected from the before-mentioned elements.

The effects described herein were given by way of example without any intention to limit the scope of what is described in this specification, and other effects may be expected from the technology disclosed herein.

The present technology is described below in further detail according to an embodiment.

(1)

A secondary battery, including:

a positive electrode;

a negative electrode; and an electrolytic solution containing at least one of the sulfonyl compounds expressed by the following Formula (1):

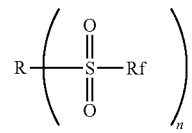

(where R represents an n-valent hydrocarbon group including one or two or more aliphatic hydrocarbon rings, Rf is one of a halogen group and a monovalent halogenated hydrocarbon group, n is an integer greater than or equal to 1, and the n-valent hydrocarbon group may include one or two or more aromatic hydrocarbon rings, provided that a ring closest to a sulfur atom (S) forming a sulfonyl group ($-S(=O)_2-$) is an aliphatic hydrocarbon ring).

(2)

The secondary battery recited in (1), in which the n-valent hydrocarbon group does not include the one or two or more aromatic hydrocarbon rings.

(3)

The secondary battery recited in (1) or (2), in which, in the Formula (1), the sulfur atom is bonded to a carbon atom (C) forming the aliphatic hydrocarbon ring.

(4)

The secondary battery recited in any one of (1) to (3), in which the n-valent hydrocarbon group is at least one selected from:

(A) n-valent group including one monocyclic aliphatic hydrocarbon ring;

(B) n-valent group including one polycyclic aliphatic hydrocarbon ring;

(C) n-valent group in which two or more monocyclic aliphatic hydrocarbon rings are bonded to each other;

(D) n-valent group in which two or more polycyclic aliphatic hydrocarbon rings are bonded to each other;

(E) n-valent group in which one or more monocyclic aliphatic hydrocarbon rings and one or more polycyclic aliphatic hydrocarbon rings are bonded to each other;

(F) n-valent group in which one or more monocyclic aliphatic hydrocarbon rings and one or more aliphatic hydrocarbon chains are bonded to each other;

(G) n-valent group in which one or more polycyclic aliphatic hydrocarbon rings and one or more aliphatic hydrocarbon chains are bonded to each other; and (H) n-valent group in which one or more monocyclic aliphatic hydrocarbon rings, one or more polycyclic aliphatic hydrocarbon rings, and one or more aliphatic hydrocarbon chains are bonded to one another, and the aliphatic hydrocarbon chains are at least one of alkyl chains, alkenyl chains, and alkynyl chains.

(5)

The secondary battery recited in (4), in which the n-valent hydrocarbon group is an n-valent group including the one monocyclic aliphatic hydrocarbon ring, and the one monocyclic aliphatic hydrocarbon ring contains 3 or more and 12 or less carbons.

(6)

The secondary battery recited in any one of (1) to (5), in which the halogen group is at least one of a fluorine group (—F), a chlorine group (—Cl), a bromine group (—Br), and an iodine group (—I), and the monovalent halogenated hydrocarbon group is a group obtained by substituting at least one hydrogen group (—H) with the halogen group in an alkyl chain, an alkenyl chain, an alkynyl chain, a cycloalkyl group, an aryl group, and monovalent groups in which two or more different ones of the before-mentioned groups are bonded to each other.

(7)

The secondary battery recited in any one of (1) to (6), in which the monovalent halogenated hydrocarbon group is a group obtained by substituting at least one hydrogen group with the halogen group in the alkyl group, and the monovalent halogenated hydrocarbon group contains 1 or more and 4 or less carbons.

(8)

The secondary battery recited in any one of (1) to (7), in which the monovalent halogenated hydrocarbon group is a perfluoroalkyl group.

(9)

The secondary battery recited in any one of (1) to (8), in which the n is smaller than or equal to 4.

(10)

The secondary battery recited in any one of (1) to (9), in which the sulfonyl compound includes at least one of compounds expressed by the following Formulas (2) and (3):

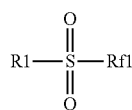

(2)

(where R1 represents a monovalent hydrocarbon group including one or two or more aliphatic hydrocarbon rings, Rf1 is one of a halogen group and a monovalent halogenated hydrocarbon group, and the monovalent hydrocarbon group may include one or two or more aromatic hydrocarbon rings, provided that a ring closest to a sulfur atom forming a sulfonyl group is an aliphatic hydrocarbon ring).

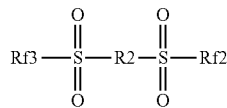

(3)

(where R2 represents a bivalent hydrocarbon group including one or two or more aliphatic hydrocarbon rings, Rf2 and Rf3 are each one of a halogen group and a monovalent halogenated hydrocarbon group, and the bivalent hydrocarbon group may include one or two or more aromatic hydrocarbon rings, provided that a ring closest to a sulfur atom forming a sulfonyl group is an aliphatic hydrocarbon ring).

(11)

The secondary battery recited in any one of (1) to (10), in which a content of the sulfonyl compound in the electrolytic solution is 0.01 wt. % or more and 5 wt. % or less.

(12)

The secondary battery recited in any one of (1) to (11), in which the secondary battery is a lithium ion secondary battery.

(13)

An electrolytic solution for secondary battery, including at least one of sulfonyl compounds expressed by the following Formula (1):

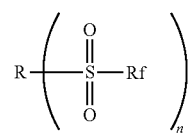

(1)

(where R represents an n-valent hydrocarbon group including one or two or more aliphatic hydrocarbon rings, Rf is one of a halogen group and a monovalent halogenated hydrocarbon group, n is an integer greater than or equal to 1, and the n-valent hydrocarbon group may include one or two or more aromatic hydrocarbon rings, provided that a ring closest to a sulfur atom forming a sulfonyl group is an aliphatic hydrocarbon ring).

(14)

A battery pack, including:

the secondary battery recited in any one of (1) or (12);

a controller that controls an operation of the secondary battery; and a switch unit that changes the operation as prompted by the controller.

(15)

An electrically driven vehicle, including:

the secondary battery recited in any one of (1) or (12);

a converter that converts electric power supplied from the secondary battery into a driving force;

a driver driven in accordance with the driving force; and a controller that controls an operation of the secondary battery.

(16)

A power storage system, including:

the secondary battery recited in in any one of (1) or (12);

one or two or more electric devices that receive electric power from the secondary battery; and a controller that controls the power supply operation for the electric devices from the secondary battery.

(17)

An electrically driven tool, including:

the secondary battery recited in in any one of (1) or (12); and a movable part that receives electric power from the secondary battery.

(18)

An electronic device including the secondary battery recited in in any one of (1) or (12) as a power supply.

This application claims the benefit of priority to and incorporates herein by reference in its entirety Japanese Patent Application No. 2016-218625 filed with Japanese Patent Office on Nov. 9, 2016.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A secondary battery, comprising:
   a positive electrode;
   a negative electrode; and
   an electrolytic solution including at least one of sulfonyl compounds expressed by chemical formula (1):

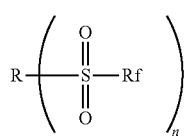

wherein R represents an n-valent hydrocarbon group including one or two or more aliphatic hydrocarbon rings, Rf includes one of a halogen group and a monovalent halogenated hydrocarbon group, n is an integer greater than or equal to 1,
   wherein the n-valent hydrocarbon group further includes one or two or more aromatic hydrocarbon rings, and
   wherein a ring closest to a sulfur atom forming a sulfonyl group is not an aromatic hydrocarbon ring but is an aliphatic hydrocarbon ring.

2. The secondary battery according to claim 1, wherein, in the chemical formula (1), the sulfur atom is bonded to a carbon atom, and the carbon atom forms the aliphatic hydrocarbon ring.

3. The secondary battery according to claim 1, wherein the n-valent hydrocarbon group is at least one selected from:
   a n-valent group including one monocyclic aliphatic hydrocarbon ring;
   a n-valent group including one polycyclic aliphatic hydrocarbon ring;
   a n-valent group in which two or more monocyclic aliphatic hydrocarbon rings are bonded to each other;
   a n-valent group in which two or more polycyclic aliphatic hydrocarbon rings are bonded to each other;
   a n-valent group in which one or more monocyclic aliphatic hydrocarbon rings and one or more polycyclic aliphatic hydrocarbon rings are bonded to each other;
   a n-valent group in which one or more monocyclic aliphatic hydrocarbon rings and one or more aliphatic hydrocarbon chains are bonded to each other;
   a n-valent group in which one or more polycyclic aliphatic hydrocarbon rings and one or more aliphatic hydrocarbon chains are bonded to each other; and
   a n-valent group in which one or more monocyclic aliphatic hydrocarbon rings, one or more polycyclic aliphatic hydrocarbon rings, and one or more aliphatic hydrocarbon chains are bonded to one another, and
   wherein the aliphatic hydrocarbon chains are at least one of alkyl chains, alkenyl chains, and alkynyl chains.

4. The secondary battery according to claim 3, wherein the n-valent hydrocarbon group includes an n-valent group including one monocyclic aliphatic hydrocarbon ring, and
   the one monocyclic aliphatic hydrocarbon ring includes 3 or more and 12 or less carbons.

5. The secondary battery according to claim 1, wherein the halogen group includes at least one of a fluorine group (—F), a chlorine group (—Cl), a bromine group (—Br), and an iodine group (—I), and
   the monovalent halogenated hydrocarbon group includes a group obtained by substituting at least one hydrogen group (—H) with the halogen group in an alkyl group, an alkenyl group, an alkynyl group, a cycloalkyl group, an aryl group, and monovalent groups in which two or more different groups are bonded to each other.

6. The secondary battery according to claim 1, wherein the monovalent halogenated hydrocarbon group includes a group obtained by substituting at least one hydrogen group with the halogen group in an alkyl group, and
   the one monovalent halogenated hydrocarbon group includes 1 or more and 4 or less carbons.

7. The secondary battery according to claim 1, wherein the monovalent halogenated hydrocarbon group includes a perfluoroalkyl group.

8. The secondary battery according to claim 1, wherein the n is smaller than or equal to 4.

9. The secondary battery according to claim 1, wherein the electrolytic solution further includes a compound expressed by chemical formula (3):

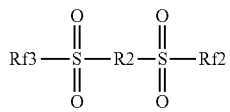

wherein R2 represents a bivalent hydrocarbon group including one or two or more aliphatic hydrocarbon rings, Rf2 and Rf3 each include one of a halogen group and a monovalent halogenated hydrocarbon group.

10. The secondary battery according to claim 1, wherein a content of the at least one of the sulfonyl compounds in the electrolytic solution is from 0.01 wt % to 5 wt %.

11. The secondary battery according to claim 1, wherein the secondary battery includes a lithium ion secondary battery.

12. The secondary battery according to claim 1, wherein the one or two or more aliphatic rings are closest to a sulfur atom forming a sulfonyl group.

13. An electrolytic solution for secondary battery, comprising at least one of sulfonyl compounds expressed by chemical formula (1):

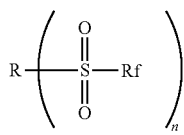

wherein R represents an n-valent hydrocarbon group including one or two or more aliphatic hydrocarbon rings, Rf includes one of a halogen group and a monovalent halogenated hydrocarbon group, n is an integer greater than or equal to 1,
   wherein the n-valent hydrocarbon group further includes one or two or more aromatic hydrocarbon rings, and
   wherein a ring closest to a sulfur atom forming a sulfonyl group is not an aromatic hydrocarbon ring but is an aliphatic hydrocarbon ring.

14. A battery pack, comprising:
a secondary battery;
a controller configured to control an operation of the secondary battery; and
a switch configured to change the operation of the secondary battery,
the secondary battery comprising:
a positive electrode;
a negative electrode; and
an electrolytic solution including at least one of sulfonyl compounds expressed by chemical formula (1):

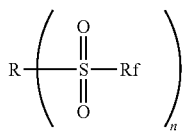

wherein R represents an n-valent hydrocarbon group including one or two or more aliphatic hydrocarbon rings, Rf includes one of a halogen group and a monovalent halogenated hydrocarbon group, n is an integer greater than or equal to 1, wherein the n-valent hydrocarbon group further includes one or two or more aromatic hydrocarbon rings, and wherein a ring closest to a sulfur atom forming a sulfonyl group is not an aromatic hydrocarbon ring but is an aliphatic hydrocarbon ring.

15. An electrically driven vehicle, comprising:
the secondary battery according to claim 1;
a converter configured to convert electric power supplied from the secondary battery into a driving force;
a driver driven in accordance with the driving force; and
a controller configured to control an operation of the secondary battery.

16. A power storage system, comprising:
the secondary battery according to claim 1;
one or two or more electric devices configured to receive electric power from the secondary battery; and
a controller configured to control power supply operation from the secondary battery to the electric devices.

17. An electrically driven tool, comprising:
the secondary battery according to claim 1; and
a movable part configured to receive electric power from the secondary battery.

18. An electronic device, comprising the secondary battery according to claim 1 as a power supply.

* * * * *